( 12 ) United States Patent
Yu et al.

(10) Patent No.: US 11,539,006 B2
(45) Date of Patent: Dec. 27, 2022

(54) ORGANOMETALLIC COMPLEX LUMINESCENT MATERIAL

(71) Applicant: GUANGDONG AGLAIA OPTOELECTRONIC MATERIALS CO., LTD, Guangdong (CN)

(72) Inventors: Mingquan Yu, Foshan (CN); Lei Dai, Foshan (CN); Lifei Cai, Foshan (CN)

(73) Assignee: GUANGDONG AGLAIA OPTOELECTRONIC MATERIALS CO., LTD, Foshan (CN)

( * ) Notice: Subject to any disclaimer, the term of this patent is extended or adjusted under 35 U.S.C. 154(b) by 368 days.

(21) Appl. No.: 16/759,983

(22) PCT Filed: Sep. 25, 2018

(86) PCT No.: PCT/CN2018/107204
§ 371 (c)(1),
(2) Date: Apr. 28, 2020

(87) PCT Pub. No.: WO2019/085682
PCT Pub. Date: May 9, 2019

(65) Prior Publication Data
US 2020/0287145 A1    Sep. 10, 2020

(30) Foreign Application Priority Data

Nov. 2, 2017  (CN) .......................... 201711061744.4

(51) Int. Cl.
*C09K 11/06*    (2006.01)
*H01L 51/00*    (2006.01)

(52) U.S. Cl.
CPC .......... *H01L 51/0087* (2013.01); *C09K 11/06* (2013.01); *C09K 2211/185* (2013.01)

(58) Field of Classification Search
CPC .. C07D 487/04; C07D 215/18; C07D 215/20; C07D 401/04; H01L 51/0087; C09K 11/06
See application file for complete search history.

(56) References Cited

U.S. PATENT DOCUMENTS

| 6,303,238 | B1 | 10/2001 | Thompson et al. |
| 6,830,828 | B2 | 12/2004 | Thompson et al. |
| 9,472,769 | B2 | 10/2016 | Yagi et al. |
| 9,825,234 | B2* | 11/2017 | Kim .................... H01L 51/0067 |
| 2003/0205707 | A1* | 11/2003 | Chi-Ming ........... H01L 51/0087 257/40 |
| 2005/0233167 | A1 | 10/2005 | Che et al. |
| 2022/0081458 | A1* | 3/2022 | Peng .................... C07F 15/0086 |

FOREIGN PATENT DOCUMENTS

| CN | 1777663 | A  | 5/2006 |
| CN | 101646746 | A | 2/2010 |
| EP | 1630217 | A1 | 3/2006 |
| JP | 2010-135689 | * | 6/2010 |
| JP | 2010-135689 | A | 6/2010 |

OTHER PUBLICATIONS

Pander, Inorg Chem, 2018, vol. 57, 3825-3832. (Year: 2018).*
"Organic electroluminescent diodes," Applied Physics Letters, vol. 51, Issue 12, p. 913 by Dr. Deng Qingyun of Kodak in 1987.

* cited by examiner

*Primary Examiner* — D Margaret M Seaman
(74) *Attorney, Agent, or Firm* — Maschoff Brennan

(57) ABSTRACT

The present invention relates to an organometal-complex luminescent material which has a structural formula (I), wherein A, B and C refer to substituted or unsubstituted C, N, O and S atoms independently; a dashed ring for linkage between A and B atoms refers to a substituted or unsubstituted conjugated ring structure; L1, L2, L3 and L4 are single bonds or double bonds independently, wherein L3 and L4 are part of the conjugated ring structure for linkage between A and B atoms; X, X1, Y and Y1 are C, N, O and S atoms independently; Ar1 and Ar2 are substituted or unsubstituted conjugated ring structures independently; M refers to Pt, W and Au atoms. An organometal complex in the luminescent material is high in fluorescence quantum efficiency and heat stability and low in quenching constant and can be used for manufacturing high-efficiency and low-efficiency roll-off red-light OLEDs.

12 Claims, 1 Drawing Sheet

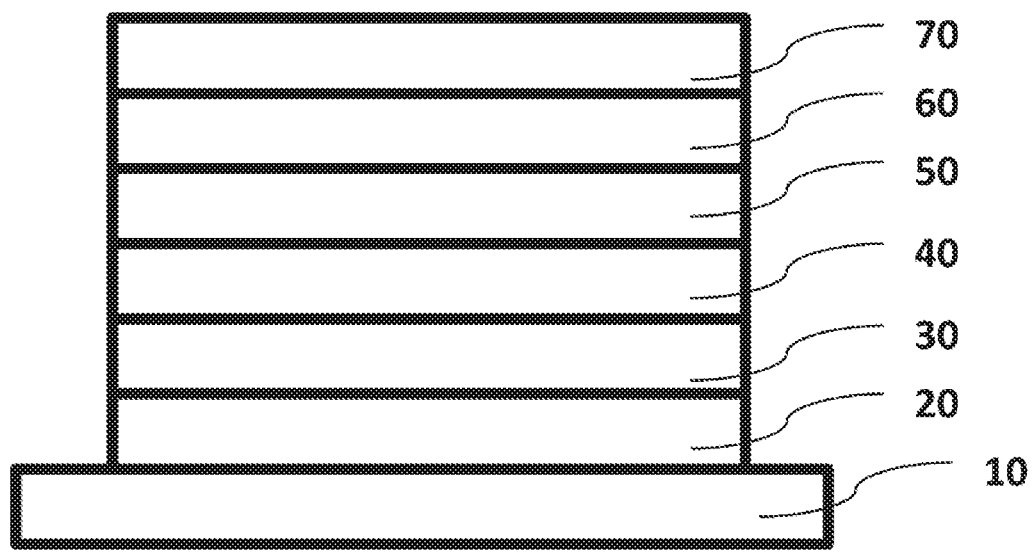

ORGANOMETALLIC COMPLEX LUMINESCENT MATERIAL

TECHNICAL FIELD

The present invention relates to an organometal-complex luminescent material, and more particularly to a dopant used in an OLED luminescent device to play a photon emission function in a luminescent layer.

BACKGROUND

The OLED (Organic Light-Emitting Diode) technology has been booming for 30 years since it was first published (organic electroluminescent diodes. Applied Physics Letters. 1987, Vol. 51, Iss. 12, Page 913) by Dr. Deng Qingyun of Kodak in 1987. In the past 5 years, the OLED technology has attracted a lot of attentions and investments from the industry due to its uniqueness. In the display field, compared with the current mainstream LCD (Liquid Crystal Display) technology, OLED display has great advantages of high brightness, high contrast, high resolution, ultra-thin display, and flexible display; in the lighting field, OLED lighting has great advantages such as high color rendering index (CRI), planar light source, and flexible light source. The OLED light-emitting technology currently faces the greatest disadvantages: high cost and short life.

An OLED device is composed of many functional layers. In a luminescent layer, a dopant that emits green light and red light has the best effect, and the most widely used is a phosphorescent material. There are currently two commonly used phosphorescent materials: an organometallic complex containing metal iridium (Ir), and an organometallic complex containing metal (Pt). Both red and green metal Ir complexes are of materials having very good properties.

Since the metal iridium has six coordination sites, the organometallic complexes containing Ir each have a stereoscopic structure of a regular octahedron. Most of organic compound ligands used to synthesize the Ir complexes have only two coordination sites, so one molecule needs to have three identical or different organic ligands. Most ligands have asymmetric structures, so when organometallic complexes of metal iridium (Ir) are synthesized, two configurations with the same molecular weight and completely different luminous properties are obtained, which are called a mer configuration and a fac configuration.

Compared with the mer configuration, the fac configuration has higher luminous efficiency, but has higher cost for separating, especially in the industrial production process. In order to solve this problem, an auxiliary ligand (U.S. Pat. No. 6,830,828) can be introduced, and the conversion rate of molecules from the mer configuration to the fac configuration can also be improved by ultraviolet irradiation.

Metal platinum has four coordination sites, which can be formed into a unique configuration by designing tetradentate ligands, such that the formation of isomers can be completely avoided. Mark et al. used porphyrin as a ligand to form a Pt organometallic complex with a unique configuration (U.S. Pat. No. 6,303,238), but this complex had a poor luminous effect, and the quantum efficiency of a device was less than 1%. Chi et al. designed a series of tetradentate ligands with a Schiff base structure (US20050233167), of which the luminescence covers wavelength bands from green to red. However, the fluorescent quantum efficiency of red light molecules is still low (about 40%).

SUMMARY

In view of the defects in the above fields, the present invention provides a novel quadridentate organometallic complex luminescent material, which has a more rigid configuration and can be used to manufacture high-efficiency red OLEDs.

The present invention further provides a preparation method for the luminescent material.

The present invention further provides a luminescent device prepared from the luminescent material.

An organometal-complex luminescent material has a structure as shown in formula I,

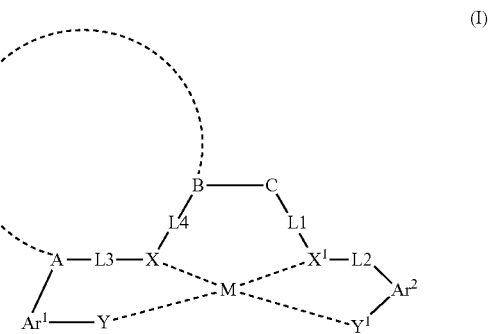

(I)

wherein A, B and C refer to substituted or unsubstituted C, N, O and S atoms independently;

a dashed ring for linkage between A and B atoms refers to a substituted or unsubstituted conjugated ring structure;

L1, L2, L3 and L4 are single bonds or double bonds independently, wherein L3 and L4 are part of the conjugated ring structure;

X, X1, Y and Y1 are C, N, O and S atoms independently;

Ar1 and Ar2 are a substituted or unsubstituted conjugated ring structure independently;

M refers to Pt, W and Au atoms;

the term "substituted" means being selected from, but not limited to: hydrogen, deuterium, sulfur, halogen, hydroxyl, acyl, alkoxyl, acyloxyl, amino, nitro, acylamino, cyano, carboxyl, styryl, aminocarbonyl, carbamoyl, benzylcarbonyl, aryloxyl, a saturated alkyl chain containing 1-30 C atoms, an unsaturated alkyl chain containing 1-30 C atoms, an aromatic ring containing 5-30 C atoms, and a heteroaromatic ring containing 5-30 C atoms.

the X and X1 are N atoms, the Y and Y1 are O atoms, and the M is a Pt atom.

The structure of the molecule as shown in formula (I) may preferably be the structure of formula (II),

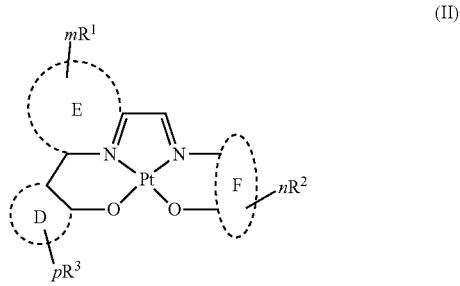

(II)

in which, m, n, and p are integers from 0 to 30; $R^1$, $R^2$, and $R^3$ are substituents other than hydrogen on the rings D, E, and F, $R^1$, $R^2$, and $R^3$ are independently selected from deuterium, sulfur, halogen, hydroxyl, acyl, alkoxyl, acyloxyl, amino, nitro, acylamino, cyano, carboxyl, styryl, aminocarbonyl, carbamoyl, benzylcarbonyl, aryloxyl, saturated alkyl containing 1-30 C atoms, unsaturated alkyl containing 1-30 C atoms, an aromatic ring group containing 5-30 C atoms, and a heteroaromatic ring group containing 5-30 C atoms; adjacent $R^1$, $R^2$, and $R^3$ can be independently connected to one another through a covalent bond to form a ring; and D and E are aromatic or heteroaryl rings each containing 5-30 C atoms; F is an aromatic or heteroaryl ring each containing 9-30 C atoms.

The D is a five- or six-membered aromatic ring or heterocyclic ring, a benzoaromatic ring or a benzohetercyclic ring; the E is a five- or six-membered heterocyclic ring or a benzohetercyclic ring; the F is a bi- or tri-cyclic aromatic ring, wherein $R^1$, $R^2$, $R^3$ are independently selected from halogen, a saturated alkyl chain containing 1-20 C atoms, an aromatic ring containing 6-20 C atoms, and a heteroaromatic ring containing 6-20 C atoms; adjacent $R^1$, $R^2$, and $R^3$ can be independently connected to one another through a covalent bond to form a ring; and m, n, and p are integers from 0 to 10.

The D is a benzene ring or a naphthalene ring, the E is a pyridine ring or a quinoline ring, and the F is a naphthalene ring or an anthracene ring, wherein $R^1$, $R^2$, $R^3$ are independently selected from halogen, a saturated alkyl chain containing 1-10 C atoms, an aromatic ring containing 6-10 C atoms, and a heteroaromatic ring containing 6-10 C atoms; adjacent $R^1$, $R^2$, and $R^3$ can be independently connected to one another through a covalent bond to form a ring; and m, n, and p are integers from 0 to 6.

The D is a benzene ring, the E is a pyridine ring, and the F is a naphthalene ring, wherein $R^1$ is hydrogen or halogen, wherein $R^2$, $R^3$ are independently selected from halogen, a saturated alkyl chain containing 1-10 C atoms, and an aromatic ring containing 6-10 C atoms; and m, n, and p are integers from 0 to 3.

For the purposes of this application, unless otherwise specified, the terms halogen, alkyl, cycloalkyl, aryl, acyl, alkoxyl, and heterocyclic aromatic systems or heterocyclic aromatic groups may have the following meanings:

the aforementioned halogen or halide includes fluorine, chlorine, bromine and iodine, preferably F, Cl, Br, particularly preferably F or Cl, and most preferably F.

The above-mentioned conjugated ring structure, aryl, aryl moiety or aromatic system includes aryl that has 6-30 carbon atoms, preferably 6-20 carbon atoms, and more preferably 6-10 carbon atoms and is composed of one aromatic ring and a plurality of fused aromatic rings. Suitable aryl is, for example, phenyl, naphthyl, acenaphthenyl, acenaphthenyl, anthryl, fluorenyl, or phenalenyl. This aryl may be unsubstituted (i.e., all carbon atoms capable of being substituted carry a hydrogen atom) or substituted at one, more than one, or all substitutable positions of the aryl. Suitable substituents are, for example, halogen, preferably F, Br or Cl; alkyl, preferably alkyl having 1-20, 1-10 or 1-8 carbon atoms, particularly preferably methyl, ethyl, isopropyl or tert-butyl; aryl, preferably re-substituted or unsubstituted $C_6$ aryl or fluorenyl; heteroaryl, preferably heteroaryl containing at least one nitrogen atom, and particularly preferably pyridyl; and alkenyl, preferably alkenyl having a double bond, and particularly preferably alkenyl having a double bond and 1-8 carbon atoms. Aryl particularly preferably has substituents selected from F and tert-butyl, preferably given aryl or aryl which is $C_6$ aryl optionally substituted with at least one of the above-mentioned substituents, wherein the $C_6$ aryl particularly preferably has 0, 1 or 2 of the above substituents; the $C_6$ aryl is particularly preferably unsubstituted phenyl or substituted phenyl, such as biphenyl, or phenyl substituted with two t-butyl groups, preferably in a meta position.

The above-mentioned alkyl or alkyl moiety includes alkyl having 1 to 20 carbon atoms, preferably 1 to 10 carbon atoms, and preferably 1 to 6 carbon atoms. The alkyl may be branched or linear, or may be cyclic, and may be interrupted by one or more heteroatoms, preferably N, O or S. Moreover, the alkyl may be substituted with one or more halogens or the above-mentioned substituents for the aryl. Similarly, in terms of alkyl, it is possible to carry one or more aryl groups. All the aforementioned aryl groups are suitable for this purpose. Alkyl is particularly preferably methyl, ethyl, isopropyl, n-propyl, isobutyl, n-butyl, tert-butyl, sec-butyl, isopentyl, cyclopropyl, cyclopentyl, cyclohexyl.

The above-mentioned acyl is connected to a CO group with a single bond, such as the alkyl as used herein.

The alkoxyl is directly connected to oxygen with a single bond, such as the alkyl as used herein.

The above heteroaromatic system or heteroaromatic group is interpreted to be related to an aromatic, $C_3$-$C_8$ cyclic group, and also contains one oxygen or sulfur atom or 1 to 4 nitrogen atoms or one oxygen or sulfur atom or a combination of at most two nitrogen atoms, and their substituted and benzopyrido-fused derivatives. For example, connected via one of ring-forming carbon atoms, the heteroaromatic system or heterocyclic aromatic group may be substituted with one or more of the mentioned substituents mentioned for the aryl.

In certain embodiments, the heteroaryl may be a five- or six-membered aromatic heterocyclic ring system carrying 0, 1 or 2 substituents. Typical examples of heteroaryl include, but are not limited to, unsubstituted furan, benzofuran, thiophene, benzothiophene, pyrrole, pyridine, indole, azole, benzoxazole, isoxazole, benzoisoazole, thiazole, benzothiazole, isothiazole, imidazole, benzimidazole, pyrazole, indazole, tetrazole, quinoline, isoquinoline, pyridazine, pyrimidine, purine and pyrazine, furan, 1,2,3-diazole, 1,2,3-thiadiazole, 1,2,4-thiadiazole, triazole, benzotriazole, pteridine, benzoxazole, diazole, benzopyrazole, quinazine, cinnoline, phthalazine, quinazole and quinoxaline and their mono- or di-substituted derivatives. In certain embodiments, the substituents are halo, hydroxyl, cyano, O—$C_{1-6}$ alkyl, $C_{1-6}$ alkyl, hydroxy $C_{1-6}$ alkyl, and amino-$C_{1-6}$ alkyl.

In order to achieve red light emission, an organometallic complex having a chemical structure of formula (II) needs a basic structure containing a Schiff base (that is, a structure formed by an N atom and an adjacent atom in the formula). It is mentioned in the background that the red light emission of Pt organometallic complexes having a Schiff base structure has the problem of low fluorescence quantum efficiency.

In order to improve the fluorescence quantum efficiency of molecules, there are two main methods: 1. introducing strong σ-donor ligands; 2. enhancing the molecular stiffness and reducing the distortion in the configuration of the molecules in an excited state (Chi, Chem. sci., 2016, 7, 1653). Without changing the electronic structure of the molecules, the increase in a conjugate area of D, E, and F rings in formula II can effectively improve the stiffness of the molecules. The vibration of the molecules designed in this way in the excited state will be limited, and the modes of electronic transition will be reduced, which can directly improve the fluorescence quantum efficiency of the molecules.

On the premise of enhancing the fluorescence quantum efficiency of the core, the quenching of triplet excitons at high exciton concentrations can be suppressed by introducing anti-aggregation groups into the D, E, and F rings. In this way, it is possible to increase the doping concentration while ensuring that the current efficiency under high operating current does not change significantly, thereby further improving the working efficiency of a device.

Specific examples shown in formula (II) include, but are not limited to, the following structures:

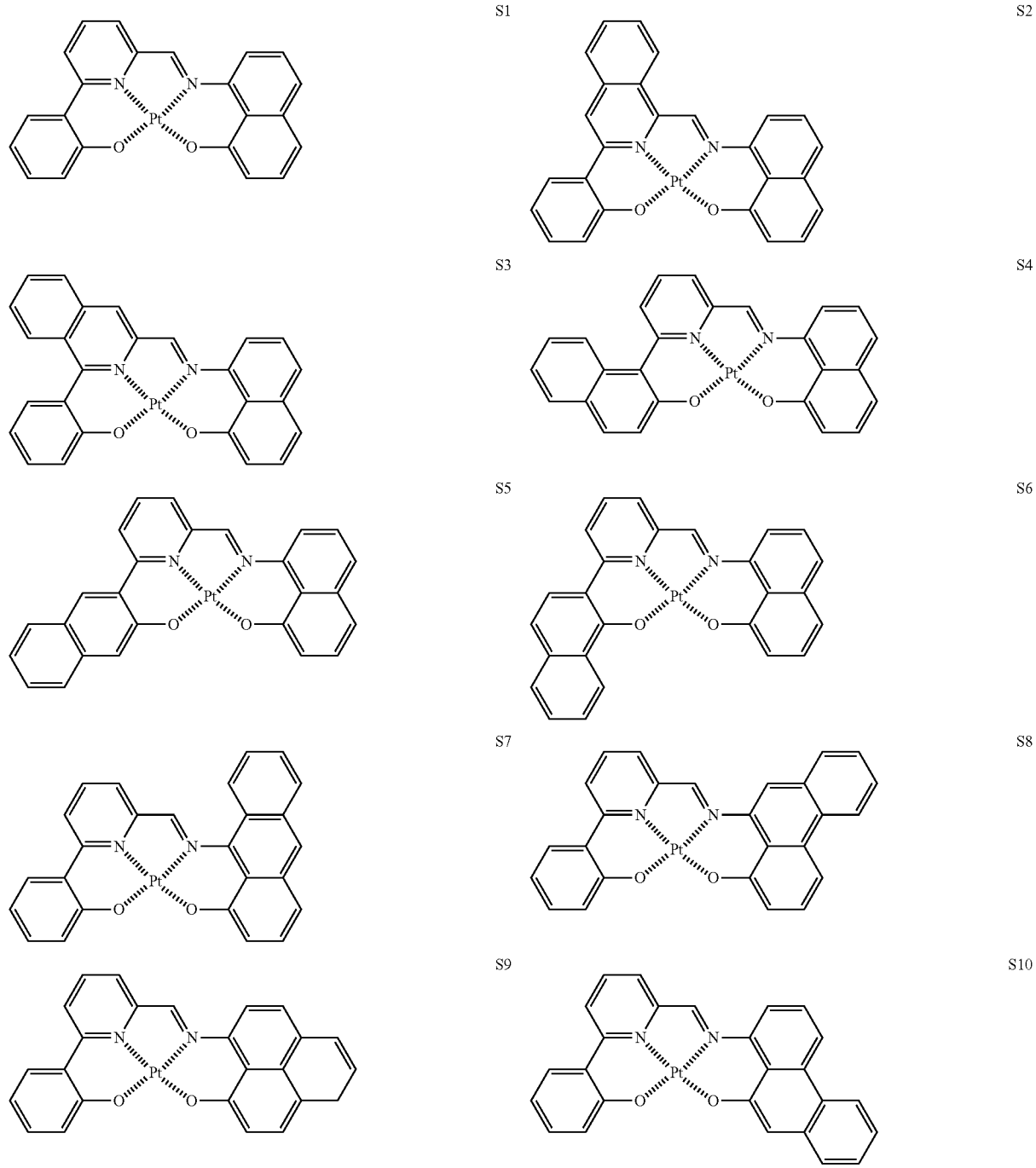

-continued
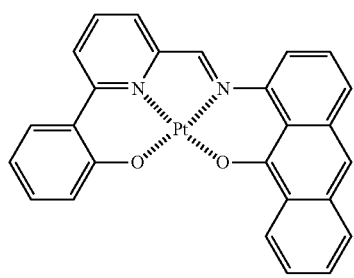
S11
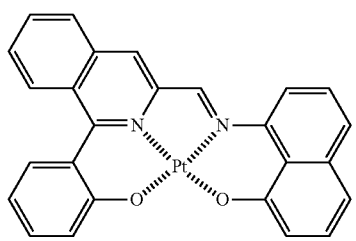
S12
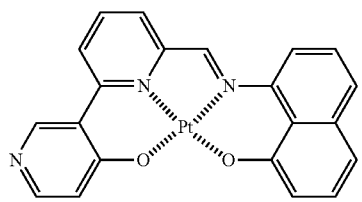
S13
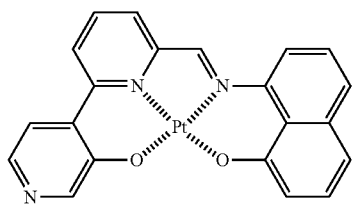
S14
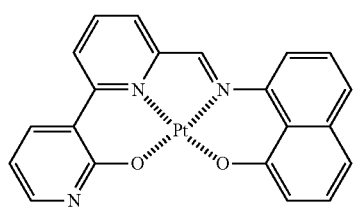
S15
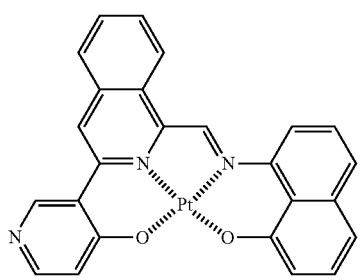
S16
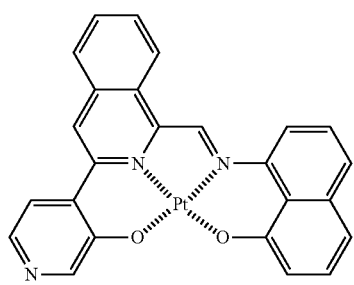
S17
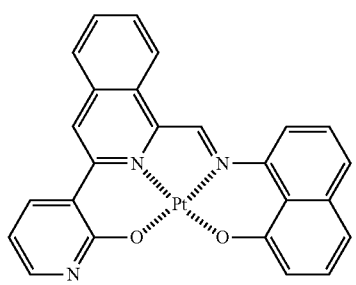
S18
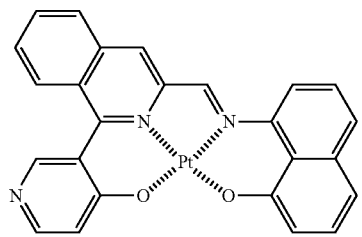
S19
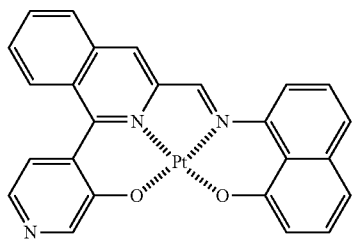
S20
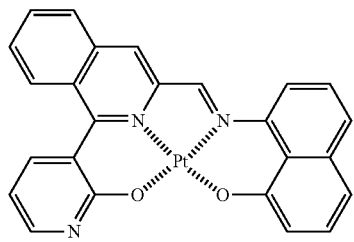
S21
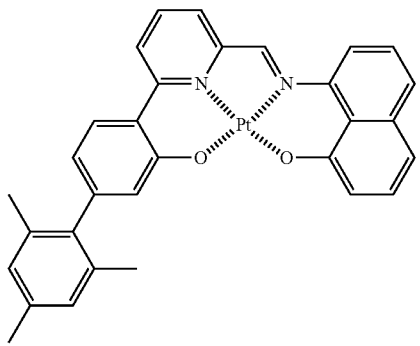
S22

-continued
S23
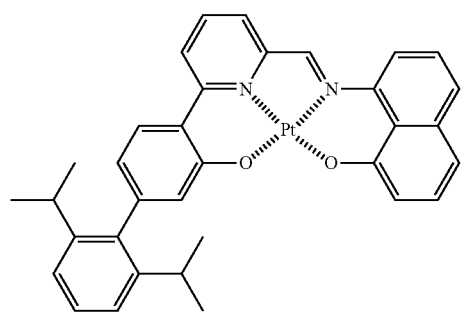
S24
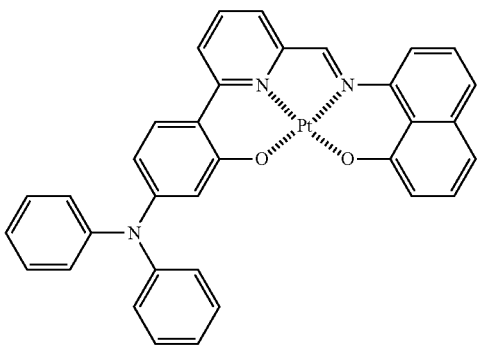
S25
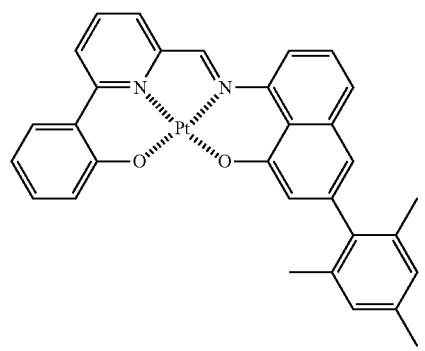
S26
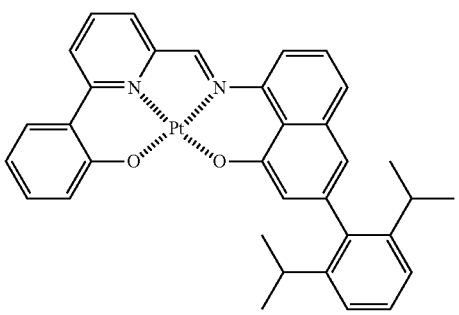
S27
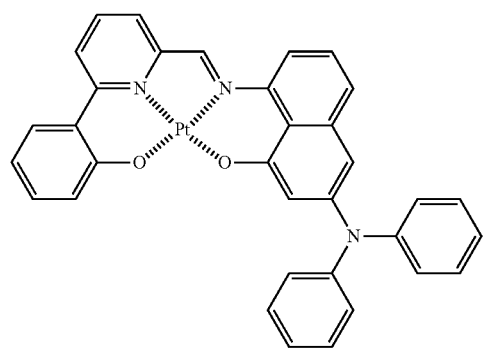
S28
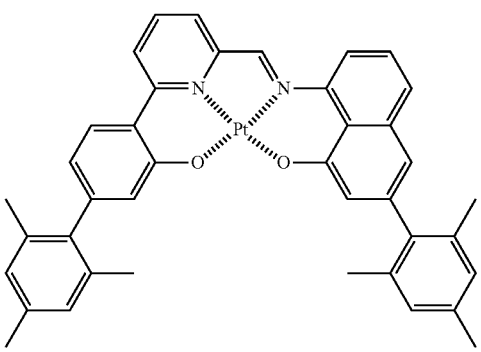
S29
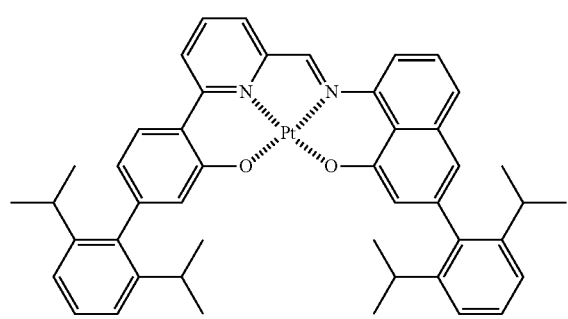
S30
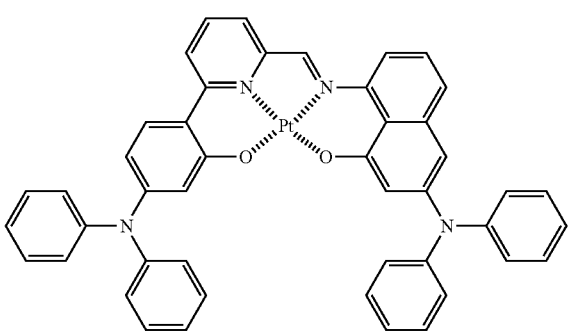

S31
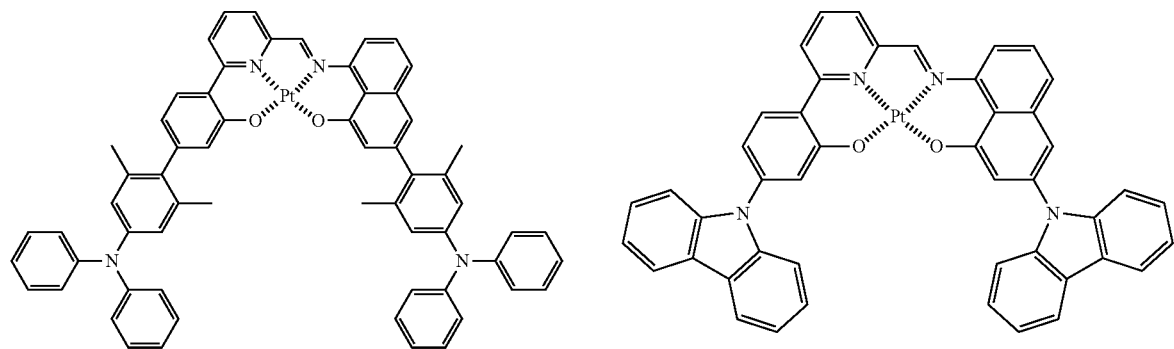
S32
S33
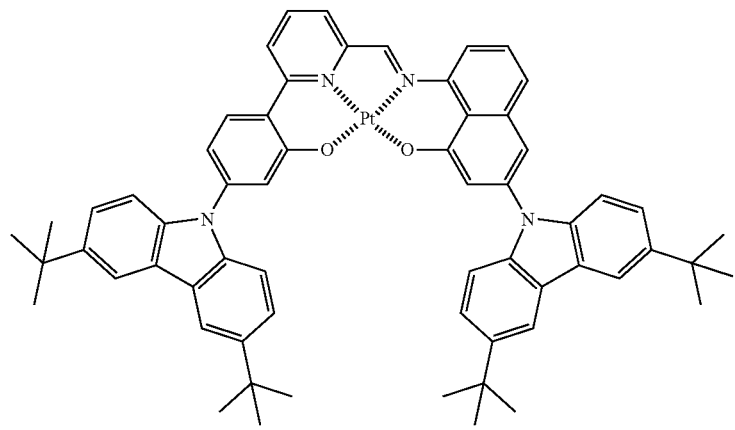
S34
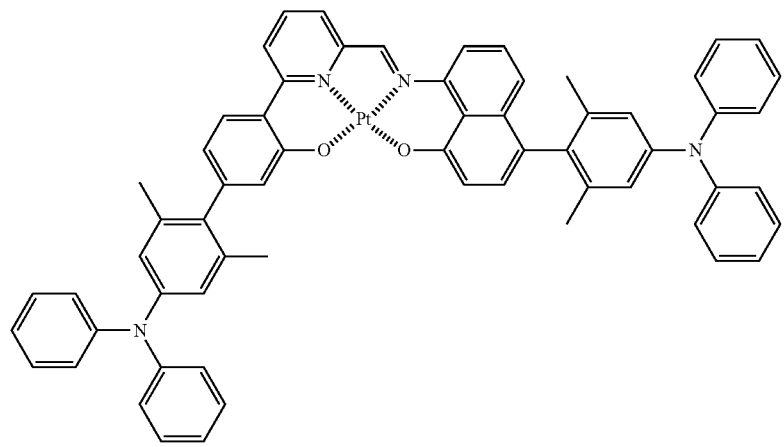
S35
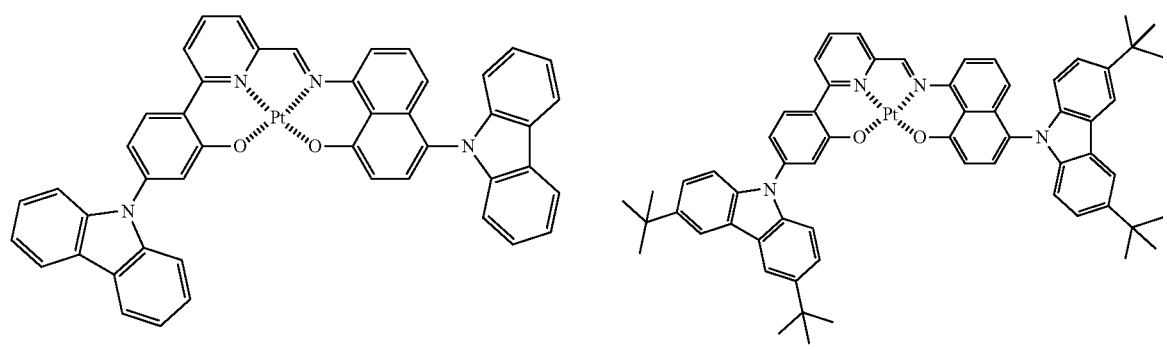
S36

-continued
S37
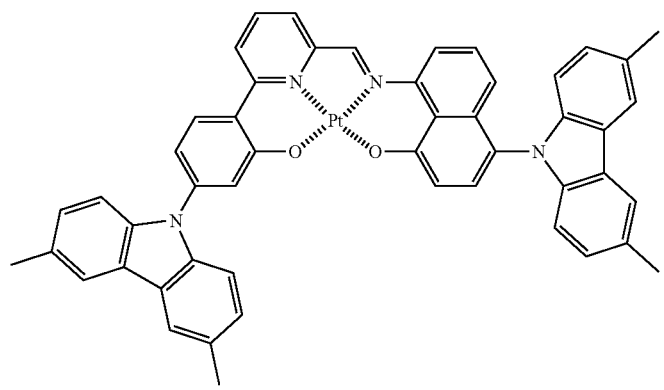
S38
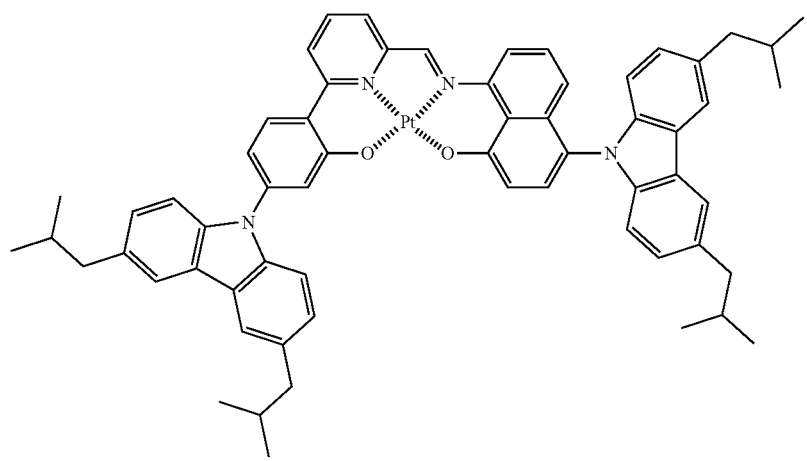
S39
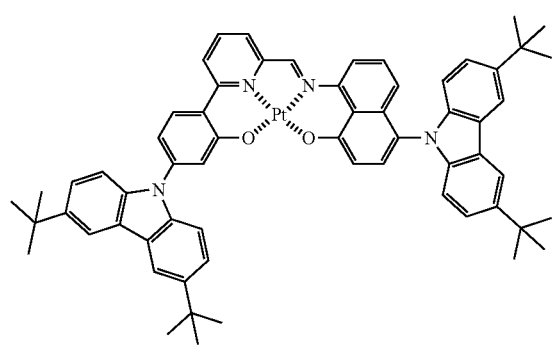
S40
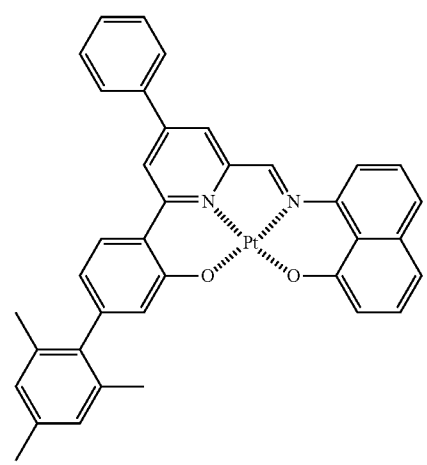

-continued
S41
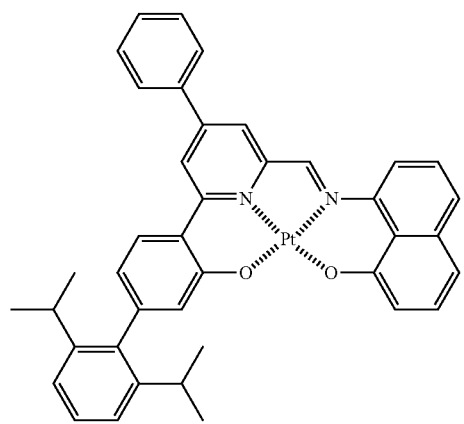
S42
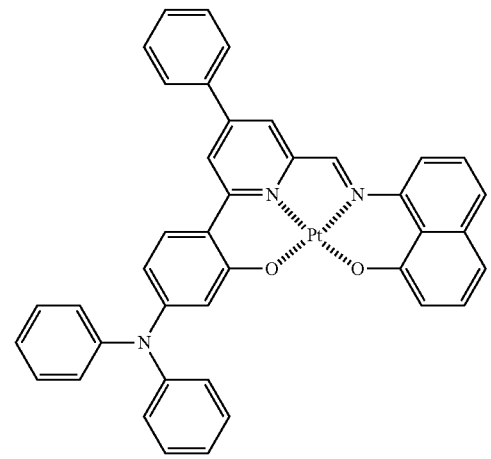
S43
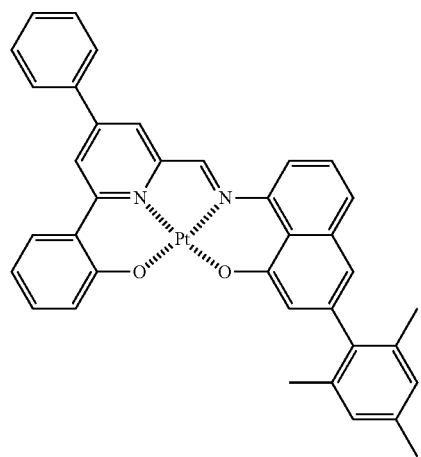
S44
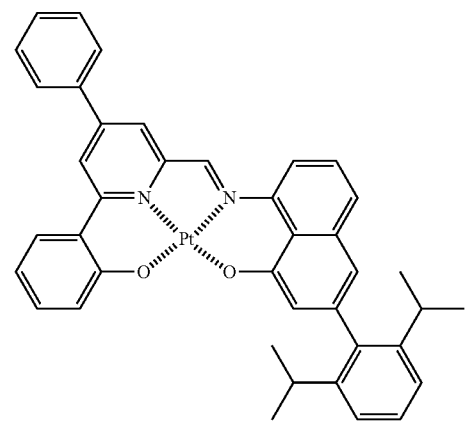
S45
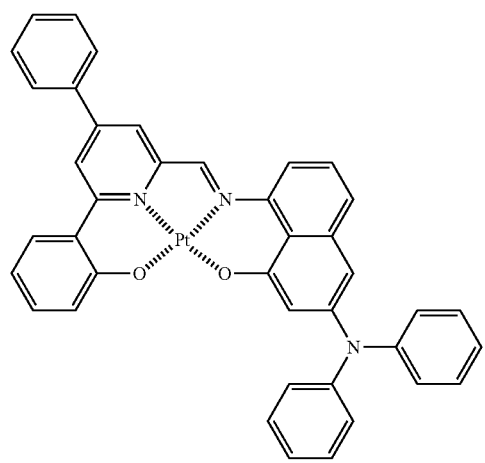
S46
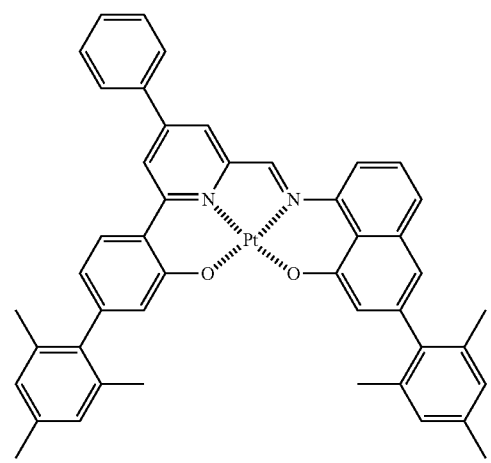

-continued
S47
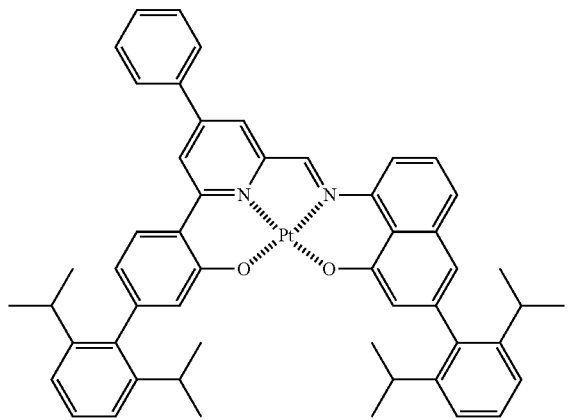
S48
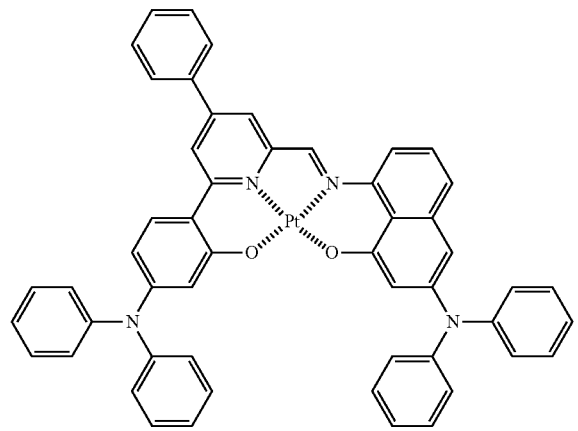
S49
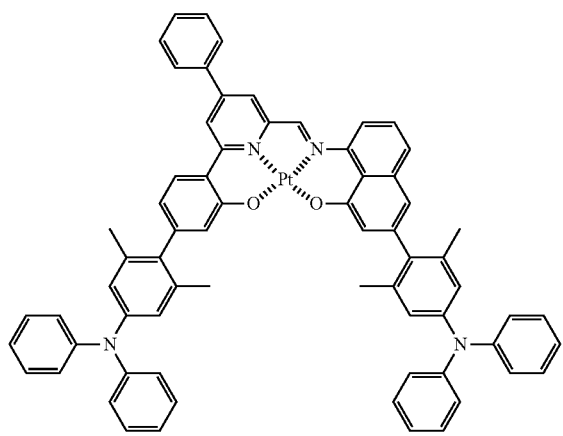
S50
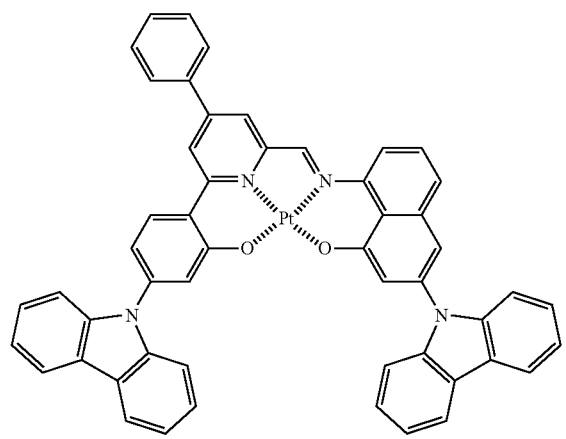
S51
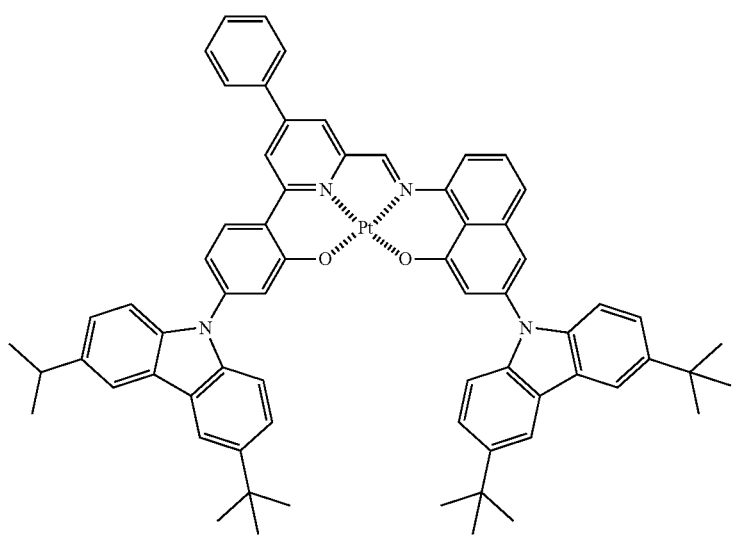

-continued
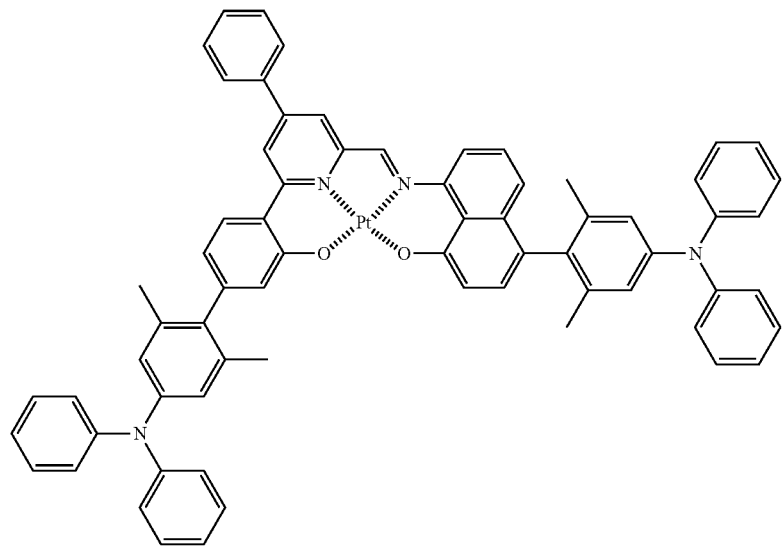
S52
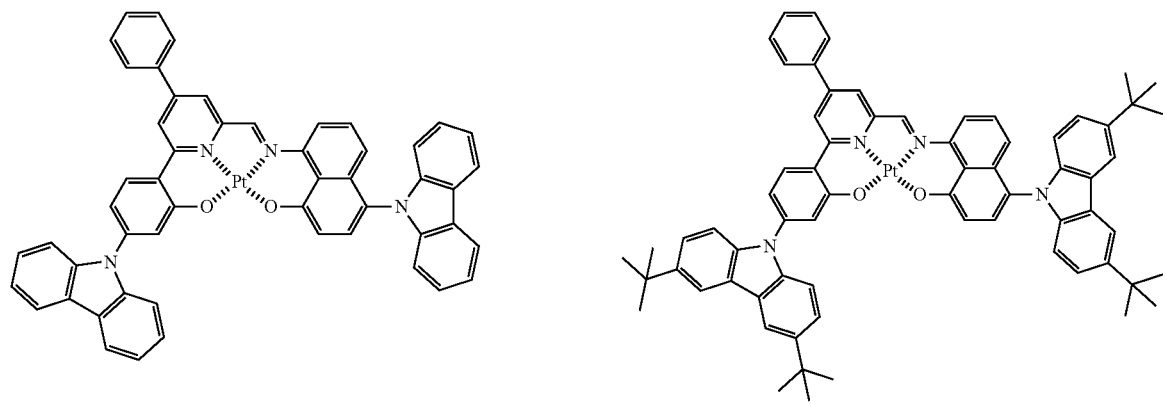
S53    S54
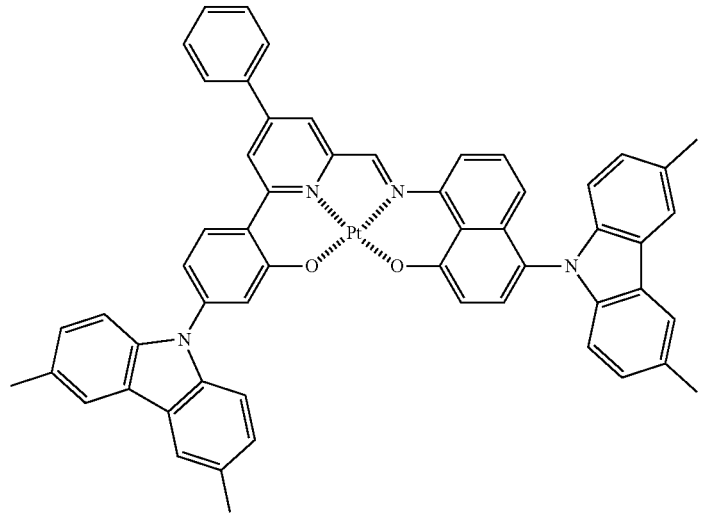
S55

S56
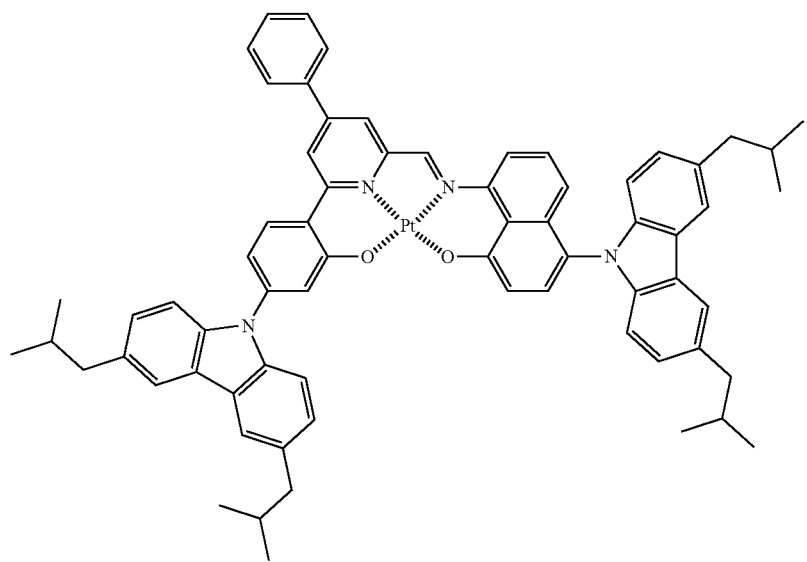
S57
S58
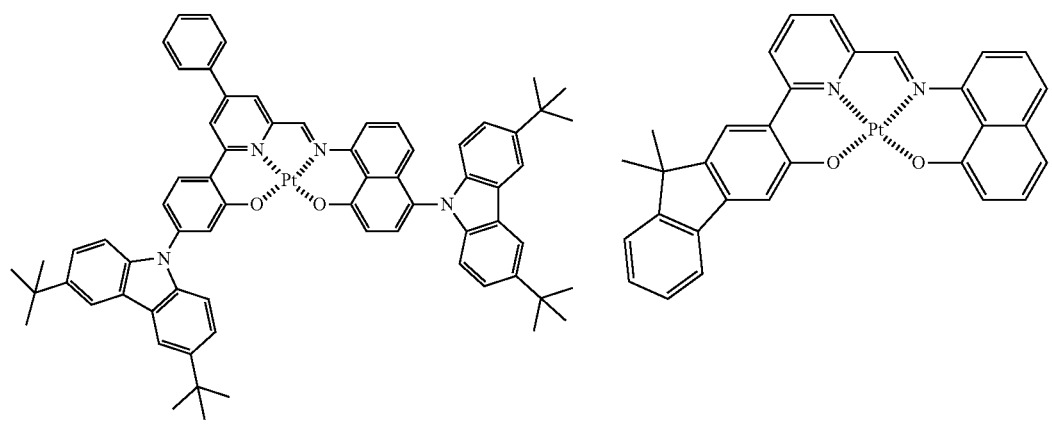
S59
S60
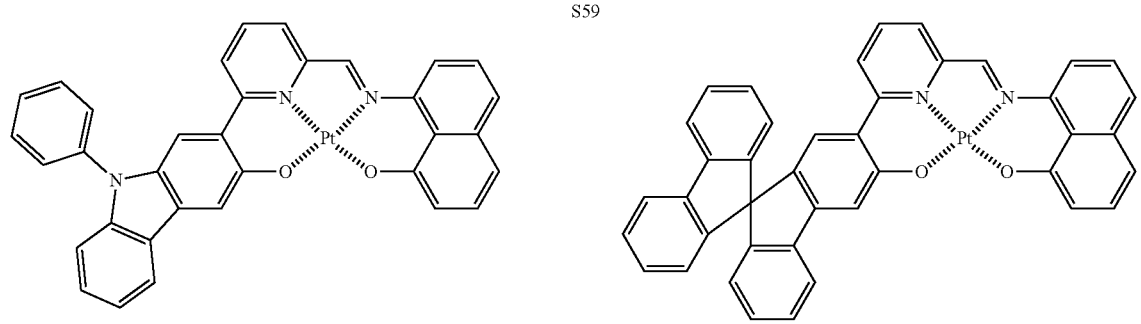

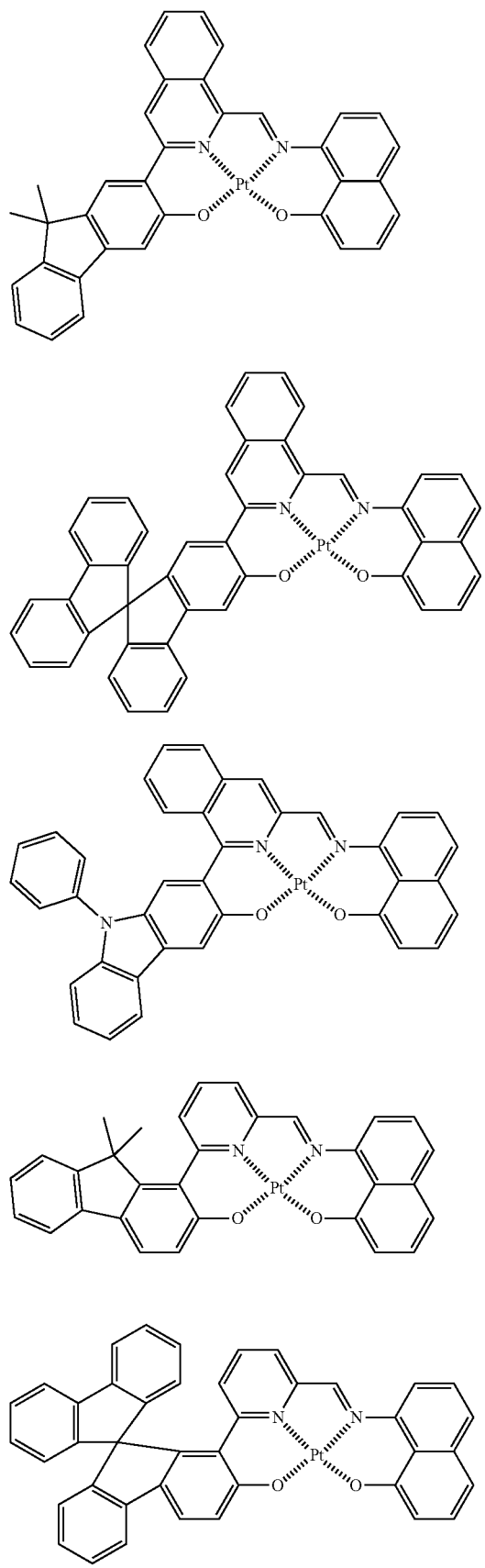

-continued
S71
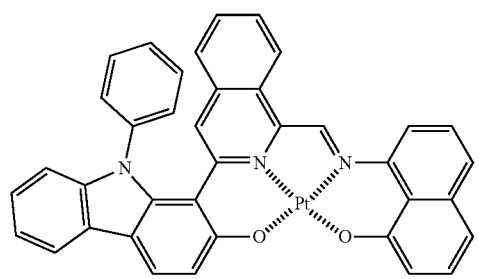
S72
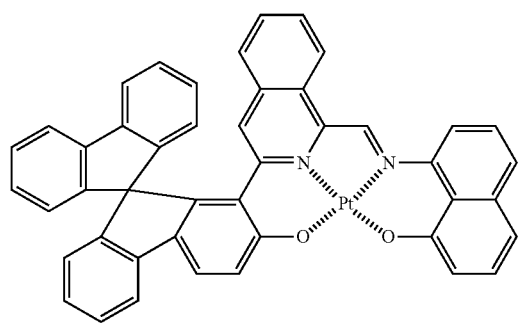
S73
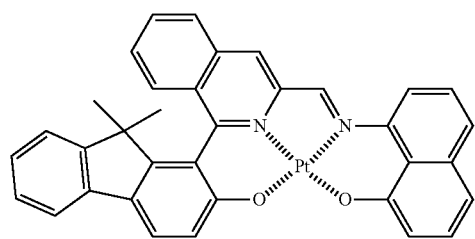
S74
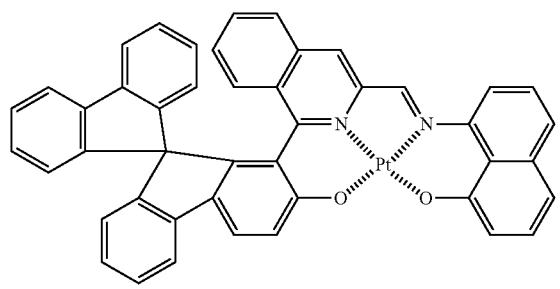
S75
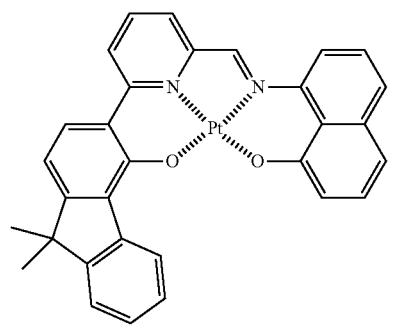
S76
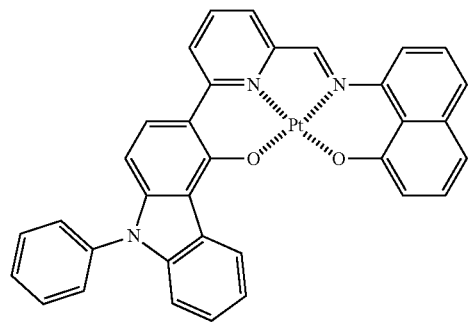
S77
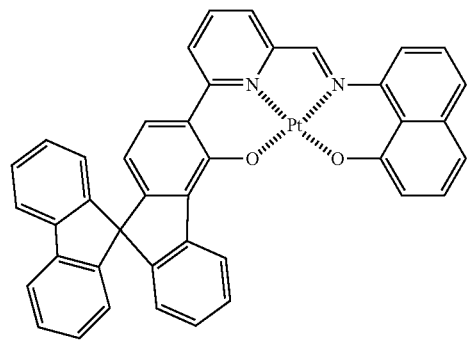
S78
S79
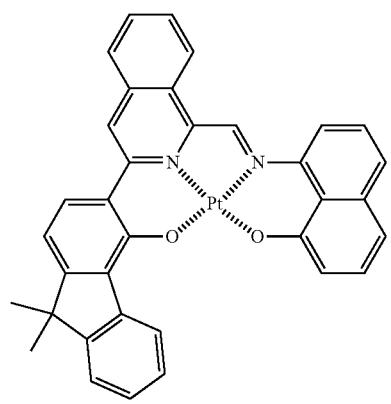
S80
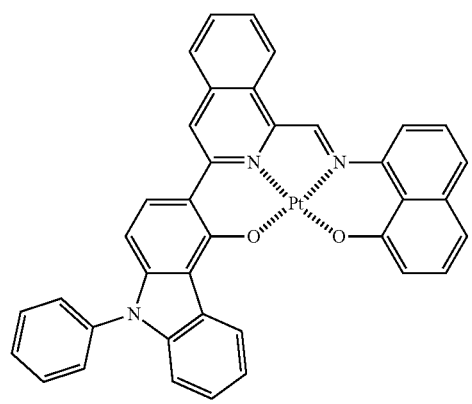

-continued
S81
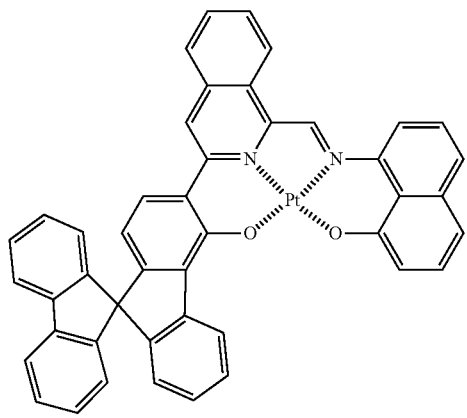
S82
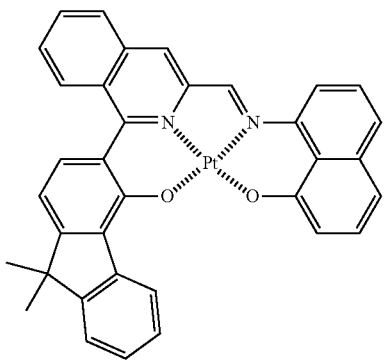
S83
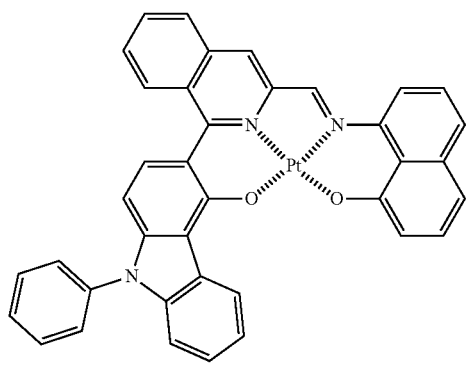
S84
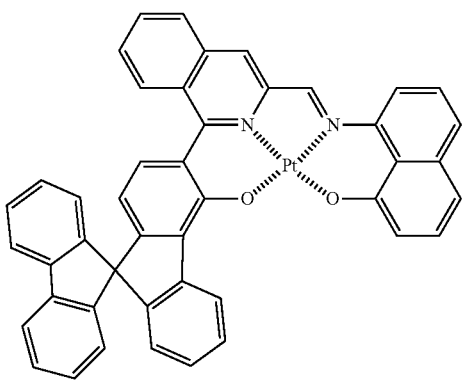
S85
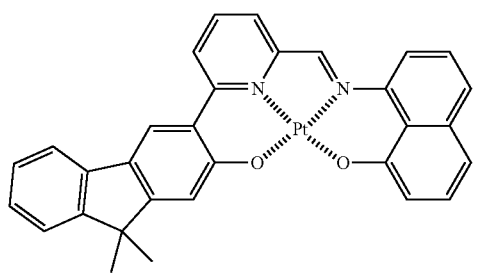
S86
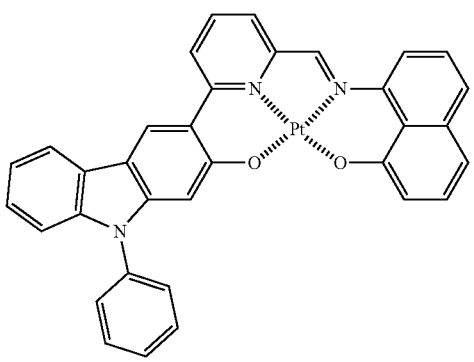
S87
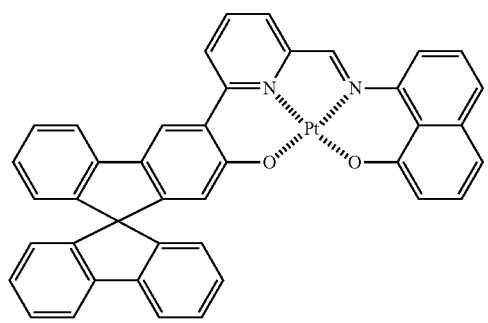
S88
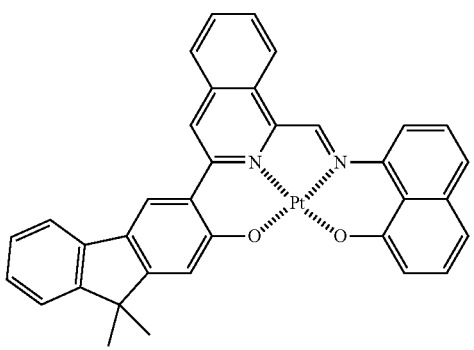

-continued
S89
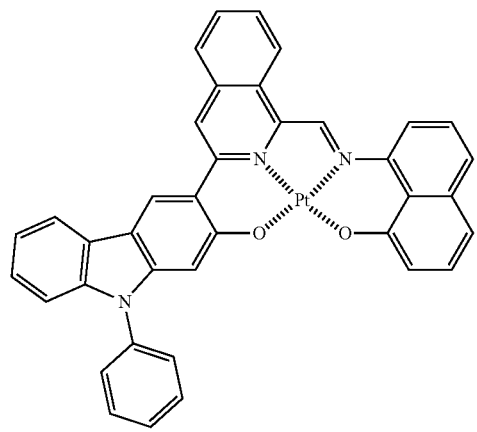
S90
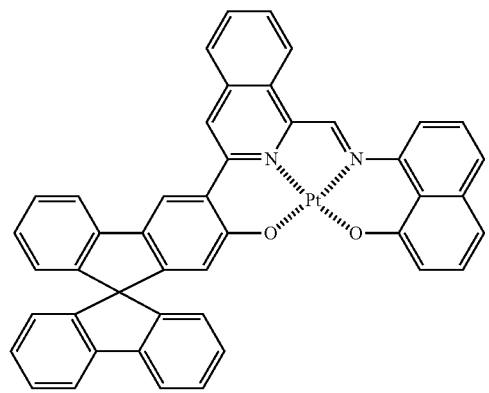
S91
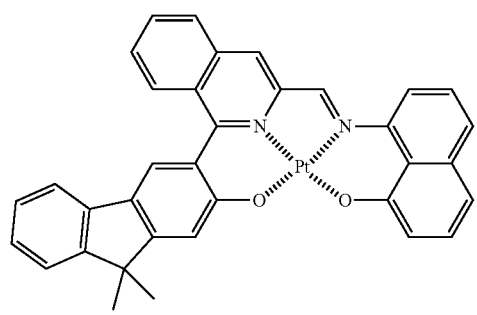
S92
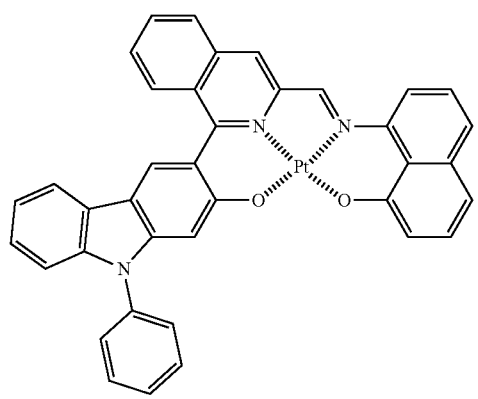
S93
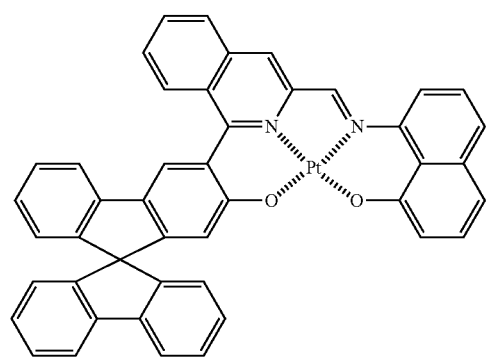
S94
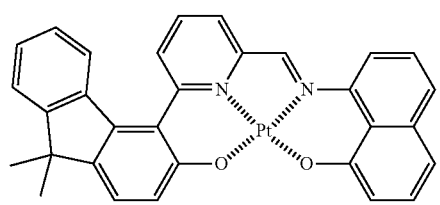
S95
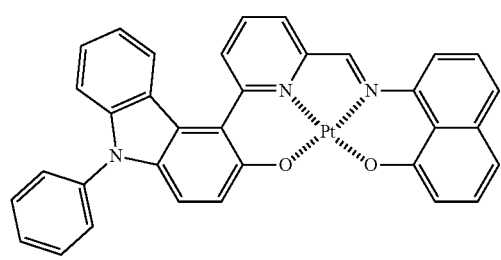
S96
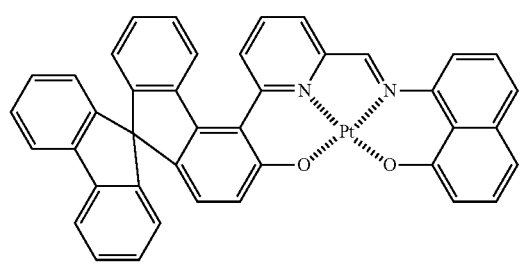

-continued
S97
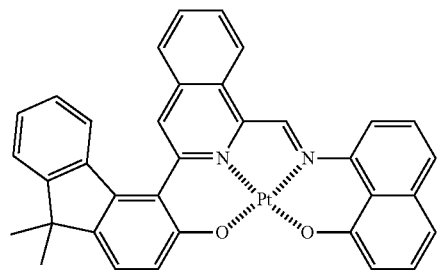
S98
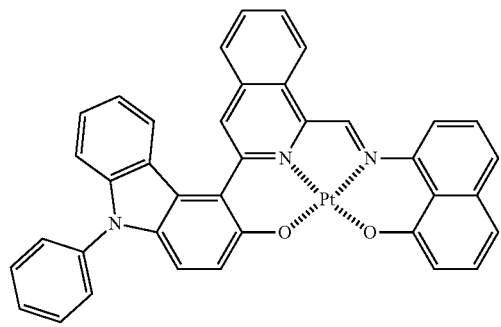
S99
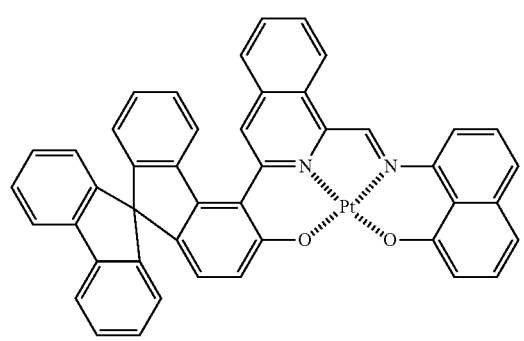
S91
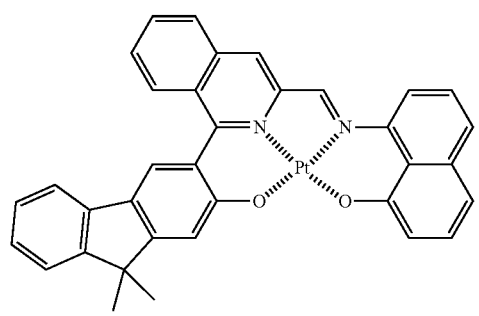
S92
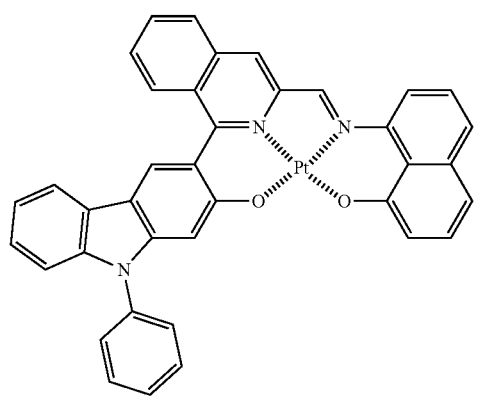
S93
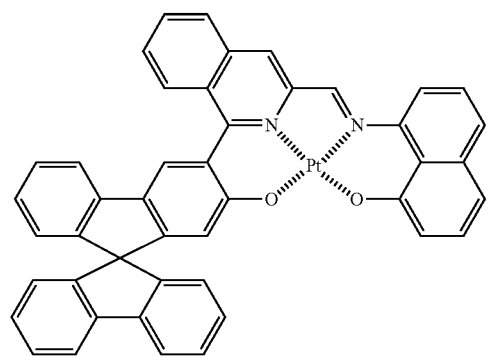
S94
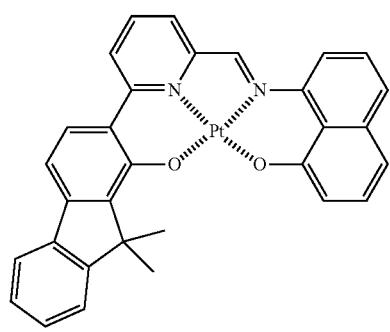

S95
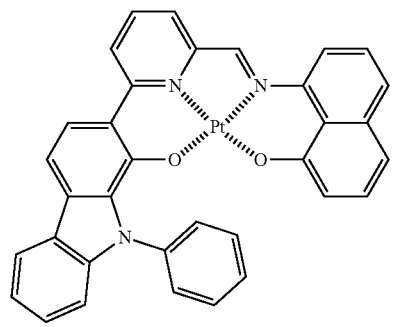
S96
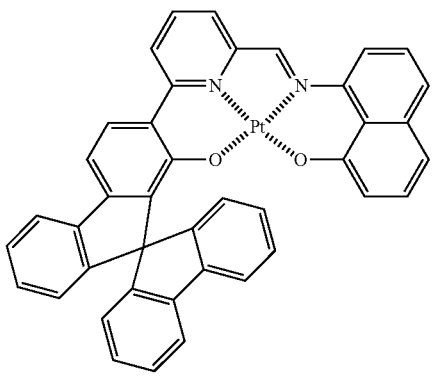
S97
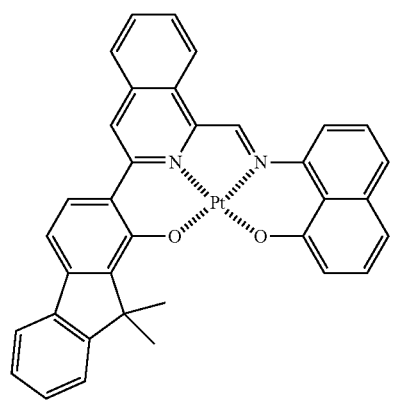
S98
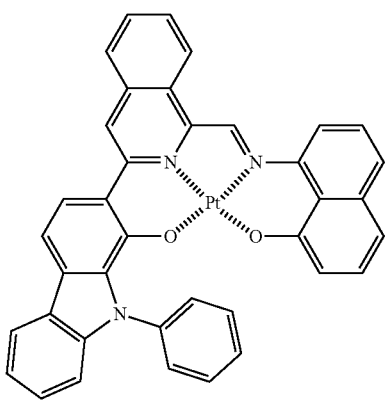
S99
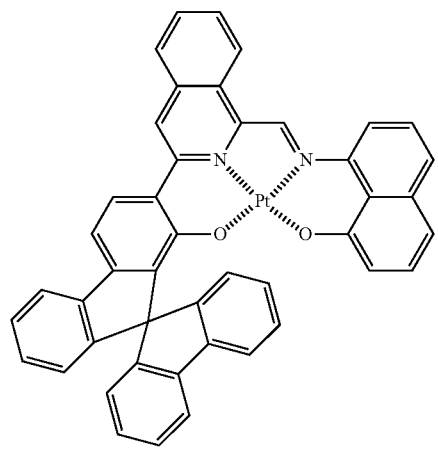
S100
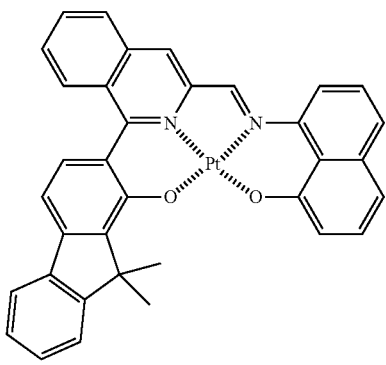
S101
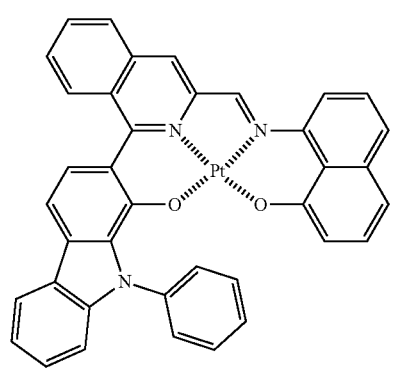
S102
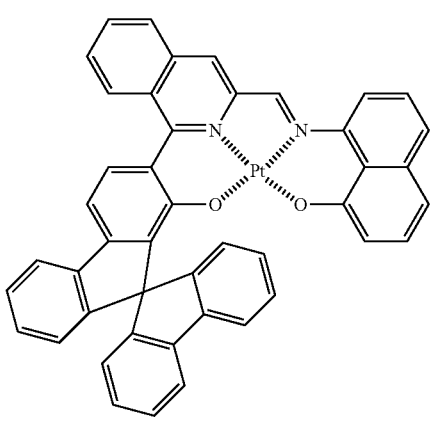

The organometallic complex having the structure (II) can be used to manufacture thermally deposited and solution-treated OLEDs.

An organic light-emitting device including one or more luminescent materials for a light-emitting diode as described in claim 1 is provided.

The light-emitting material for the light-emitting diode is applied in layers in the device by thermal deposition.

The light-emitting material for the light-emitting diode is applied in layers in the device by spin coating.

The light-emitting material for the light-emitting diode is applied in layers in the device by ink-jet printing.

The above organic light-emitting device emits a monochromatic-red color when a current is applied to the layers.

An organometal complex in the present invention is high in fluorescence quantum efficiency and heat stability and low in quenching constant and can be used for manufacturing high-efficiency and low-efficiency roll-off red-light OLEDs.

BRIEF DESCRIPTION OF THE DRAWINGS

Detailed Description

The present invention will be further described in detail with reference to the following embodiments.

Embodiment 1

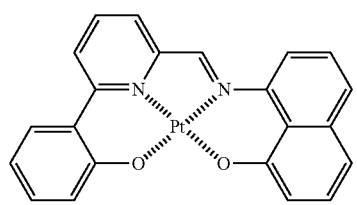

(S1)

Preparation of Molecules

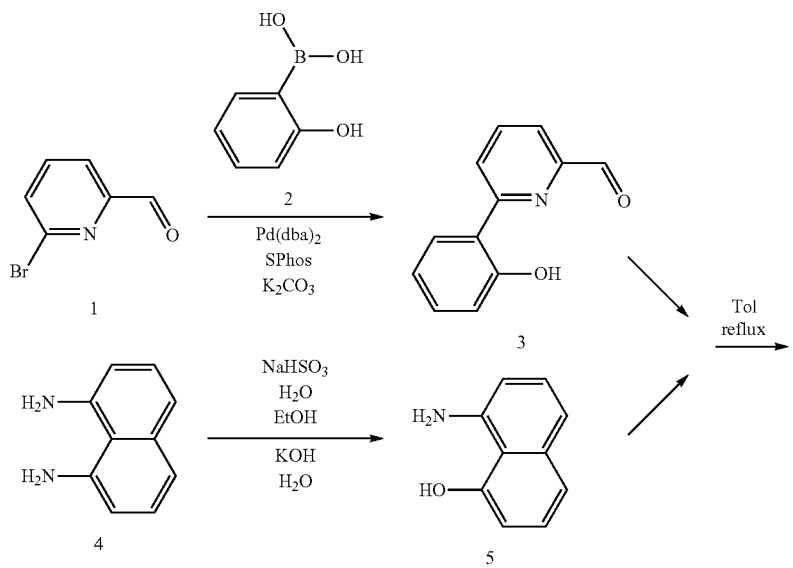

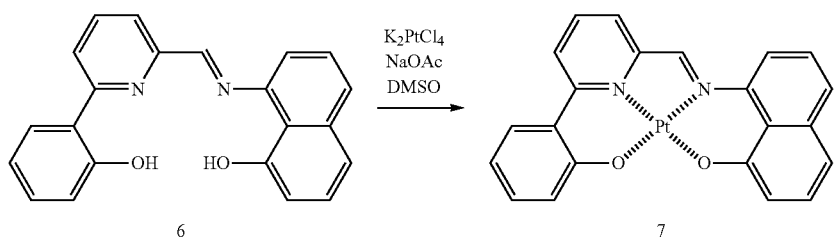

Compounds 1, 2, 4 and the inorganic salts, catalysts, catalyst ligands, and solvents used in the reaction are all commercially available raw materials.

Synthesis of compound 3: 18.6 g (0.1 mol) of compound 1 and 15.2 g (0.11 mol) of compound 2 are added to a round-bottom flask. 0.575 g (0.001 mol) of Pd (dba)$_2$ and 0.82 g (0.002 mol) of SPhos are added, vaccumized for 30 minutes, and then filled with nitrogen for protection; 400 ml of toluene is bubbled with nitrogen for 30 min, and then added to the flask; 150 ml of potassium carbonate aqueous solution having a concentration of 2M is bubbled with nitrogen for 30 minutes, and then added to the flask. The mixture is reacted for 12 hours under a nitrogen atmosphere, cooled, washed with water, dried over anhydrous magnesium sulfate, and filtered. After a toluene solvent is distilled off from the organic phase, the solid is recrystallized with a n-hexane/dichloromethane system. 18.3 g of pale yellow solid is obtained with a yield of 92%. Mass spectrum (APCI)m/z: 199.

Synthesis of compound 5: 10 g (0.063 mol) of compound 4 is dissolved in 30 ml of ethanol, added with 33.3 ml of saturated sodium bisulfite aqueous solution, and refluxed for 24 hours. 66.7 ml of potassium hydroxide aqueous solution having a concentration of 6M is added and refluxed for 2 hours. The resulting product is acidified with diluted hydrochloric acid and extracted with ethyl acetate. The organic phase is collected, dried over anhydrous magnesium sulfate, and concentrated to obtain 8.14 g of a brown-red solid with a yield of 81%. Mass spectrum (APCI)m/z: 159.

Synthesis of compound 6: 5 g (0.025 mol) of compound 3 and 4 g (0.025 mol) of compound 5 are dissolved in toluene, and refluxed for 12 hours under the protection of nitrogen, and the produced water is removed by a water separator. After cooling, the solution is dried with anhydrous magnesium sulfate, and concentrated, and then toluene is recrystallized to obtain 8.1 g of orange-red needle-like crystals with a yield of 95%. Mass spectrum (APCI)m/z: 340.

Synthesis of compound S1: 5 g (0.0147 mol) of compound 6 and 2.4 g of anhydrous sodium acetate (0.0294 mol) are dissolved in 100 ml of DMSO, stirred, and heated to 80° C. 6.10 g (0.0147 mol) of potassium tetrachloroplatinate is added, heated 120° C., and reacted for 5 hours. The reactant is added with 500 ml of water, and filtered to collect solids, and the solids are washed with water for multiple times, and rinsed with a small amount of methanol. After recrystallization of toluene, the resulting product is sublimed at 290° C. to obtain 5.48 g of dark red crystals with a total yield of 70%. Mass spectrum (APCI)m/z: 533.

Embodiment 2

(S23)

Preparation of Molecules

The preparation method is the same as that of the S molecule, with the only difference being that compound 7 is used instead of compound 2. The molecular formula of compound 7 is shown in formula (III):

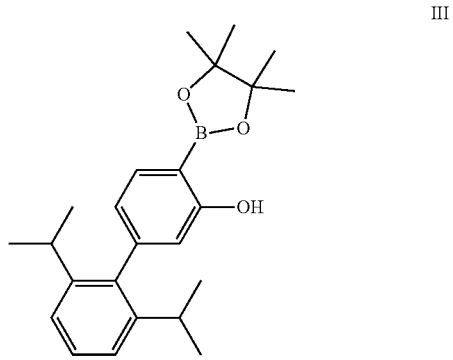 [SMILES: CC(C)c1cccc(C(C)C)c1-c1ccc(B2OC(C)(C)C(C)(C)O2)c(O)c1]

III

The synthetic route of compound 7 is as follows:

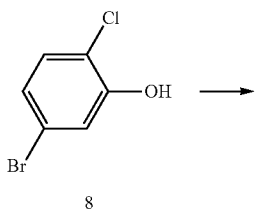

8

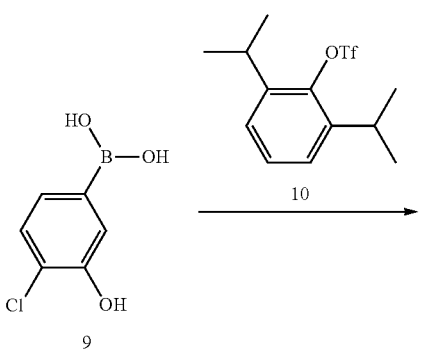

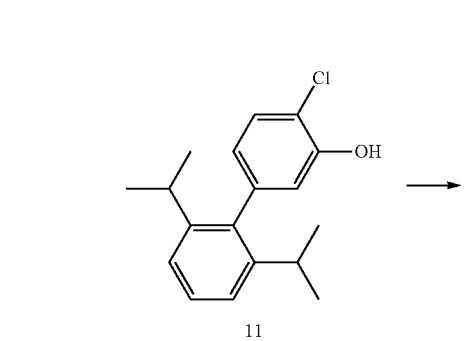

11

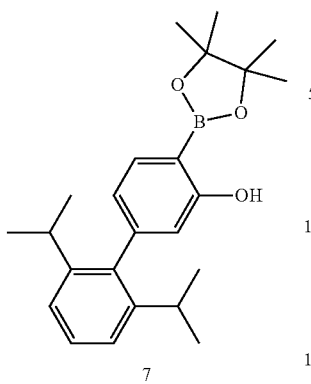

The structure of Comparative Example E1 is shown in formula (IV):

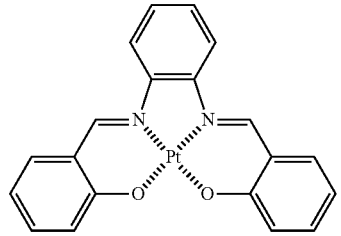

IV

The synthesis of compound E1 refers to the synthesis method in Patent US20050233167. Mass spectrometry (APCI): 510

The followings are application examples of the compound of the present invention.

A device has a structure shown in FIG. 1.

Device materials TCTA (4,4', 4"-Tri (9-carbazoyl) triphenylamine), TAPC (1,1-Bis [4-[N, N'-di (p-tolyl) amino] phenyl] cyclohexane), and TmPYPB (1,3,5-tri [(3-pyridyl)-phen-3-yl]benzene) are all commercially available materials, and their specific structures are respectively shown in formula (V):

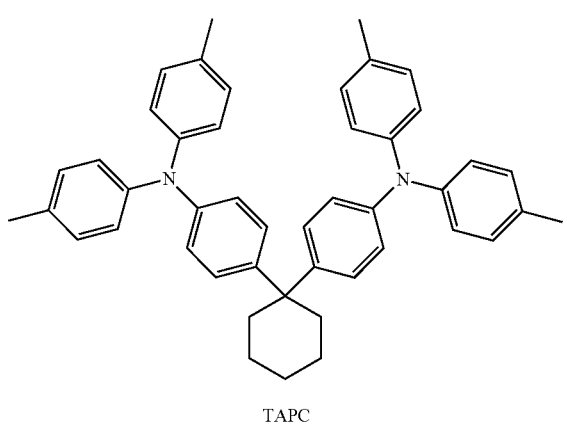

TAPC

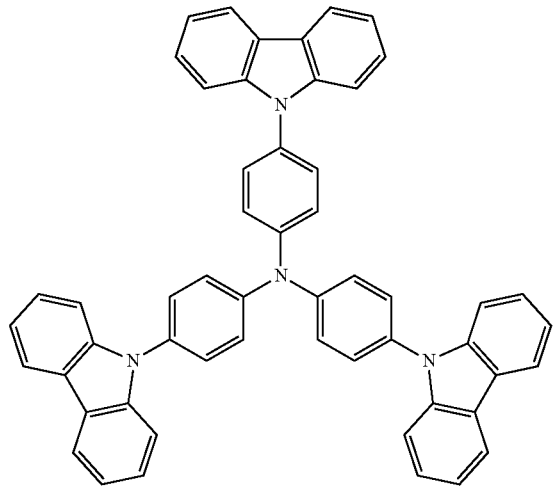

TCTA

TmPYPB

Other materials such as ITO, LiF, and Al are also commercially available materials.

The device preparation method is as follows.

First, transparent conductive ITO glass (a glass substrate 10 with an anode 20) is sequentially washed with a detergent solution, deionized water, ultrasonic cleaning with acetone, and isopropanol vapor, and then subjected to plasma treatment with oxygen for 5 minutes.

Then, 40 nm-thick TAPC is deposited on the ITO as a hole transport layer 30.

Then, a 20 nm-thick luminescent layer 40 is deposited, wherein a host material is TCTA, and an organometallic complex (dopant) with a mass concentration of 1.5% is doped.

Then, 30 nm-thick TmPYPB is deposited as an electron transport layer 50.

Finally, 1 nm-thick LiF is deposited as an electron injection layer 60 and 100 nm metal Al is deposited as a cathode 70.

The structures and manufacturing methods of the devices 1, 2, and 3 are completely the same, with the difference being that the organometallic complexes S1, S23, and E1 are sequentially used as the dopants in the luminescent layer.

The device comparison results are shown in Table 1:

|  | Device 1 | Device 2 | Device 3 |
|---|---|---|---|
| Maximum external quantum efficiency | 9.4% | 13% | 9.8% |
| External quantum efficiency at 100 mA/cm$^{-2}$ | 6% | 9% | 4.5% |
| Current efficiency at 100 mA/cm$^{-2}$ | 11.7 cd/A | 14.3 cd/A | 10.8 cd/A |
| CIE (x, y) | 0.62, 0.30 | 0.65, 0.33 | 0.65, 0.35 |

Compared with a reference device, the performances of the organic electroluminescent device prepared by the material of the present invention are improved to different extents.

The invention claimed is:

1. An organometal-complex luminescent material having a structure as shown in Formula (II),

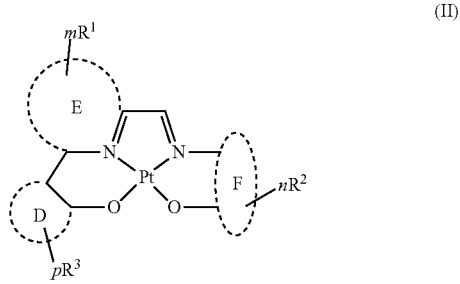

wherein:
in which, m, n, and p are integers from 0 to 30; $R^1$, $R^2$, and $R^3$ are substituents other than hydrogen on the rings D, E, and F:
$R^1$, $R^2$, and $R^3$ are independently selected from deuterium, sulfur, halogen, hydroxyl, acyl, alkoxyl, acyloxyl, amino, nitro, acylamino, cyano, carboxyl, styryl, aminocarbonyl, carbamoyl, benzylcarbonyl, aryloxyl, saturated alkyl containing 1-30 C atoms, unsaturated alkyl containing 1-30 C atoms, an aromatic ring group containing 5-30 C atoms, and a heteroaromatic ring group containing 5-30 C atoms; adjacent $R^1$, $R^2$, and $R^3$ can be independently connected to one another through a covalent bond to form a ring; and D and E are aromatic or heteroaryl rings each containing 5-30 C atoms; F is an aromatic or heteroaryl ring containing 9-30 C atoms.

2. The luminescent material according to claim 1, wherein the D is a five- or six-membered aromatic ring or heterocyclic ring, a benzoaromatic ring or a benzoheterocyclic ring; the E is a five- or six-membered heterocyclic ring or a benzoheterocyclic ring; the F is a bi- or tri-cyclic aromatic ring, wherein $R^1$, $R^2$, $R^3$ are independently selected from halogen, a saturated alkyl chain containing 1-20 C atoms, an aromatic ring containing 6-20 C atoms, and a heteroaromatic ring containing 6-20 C atoms; adjacent $R^1$, $R^2$, and $R^3$ can be independently connected to one another through a covalent bond to form a ring; and m, n, and p are integers from 0 to 10.

3. The luminescent material according to claim 2, wherein the D is a benzene ring or a naphthalene ring, the E is a pyridine ring or a quinoline ring, and the F is a naphthalene ring or an anthracene ring, wherein $R^1$, $R^2$, $R^3$ are independently selected from halogen, a saturated alkyl chain containing 1-10 C atoms, an aromatic ring containing 6-10 C atoms, and a heteroaromatic ring containing 6-10 C atoms; adjacent $R^1$, $R^2$, and $R^3$ can be independently connected to one another through a covalent bond to form a ring; and m, n, and p are integers from 0 to 6.

4. The luminescent material according to claim 3, wherein the D is a benzene ring, the E is a pyridine ring, and the F is a naphthalene ring, wherein $R^1$ is hydrogen or halogen, wherein $R^2$, $R^3$ are independently selected from halogen, a saturated alkyl chain containing 1-10 C atoms, and an aromatic ring containing 6-10 C atoms; and m, n, and p are integers from 0 to 3.

5. The luminescent material according to claim 3, wherein the formula (I) has a structure as shown in Formula (I):

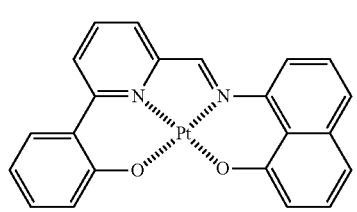

S1

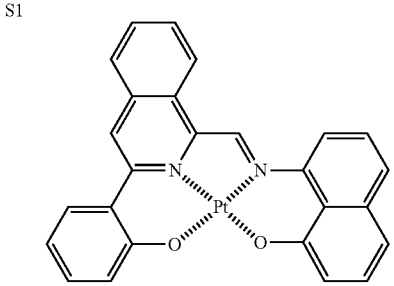

S2

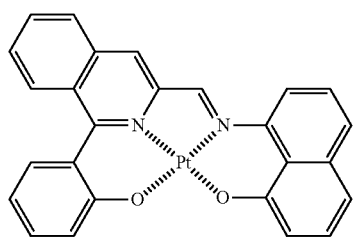

S3

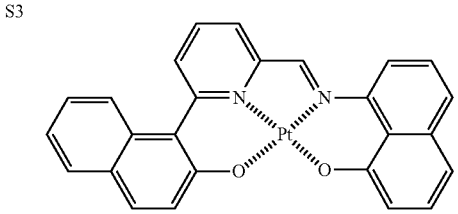

S4

-continued
S5
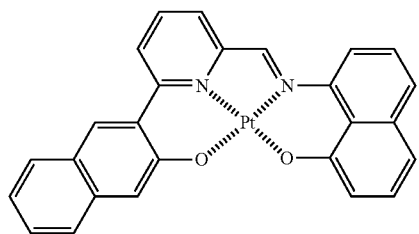
S6
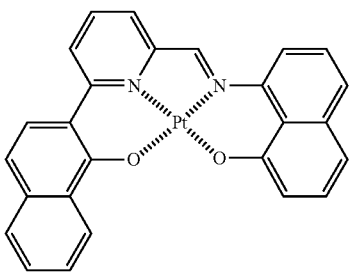
S7
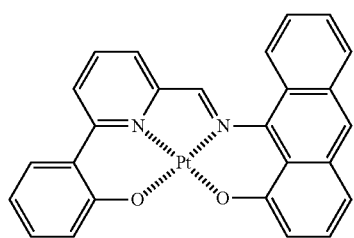
S8
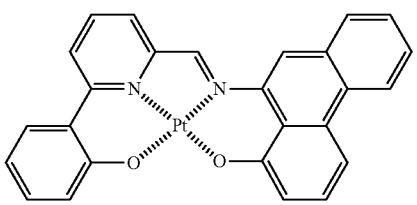
S9
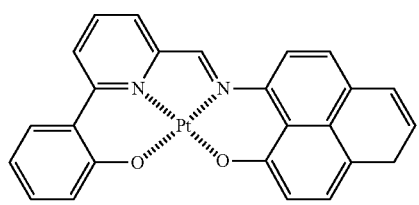
S10
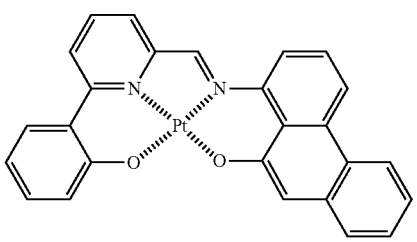
S11
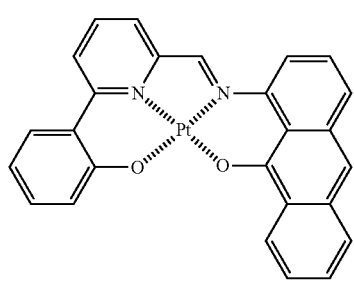
S12
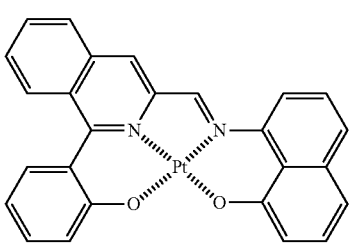
S13
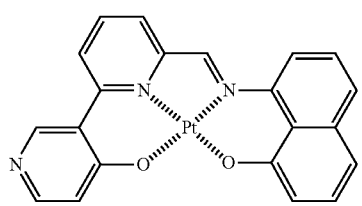
S14
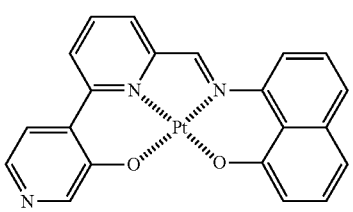
S15
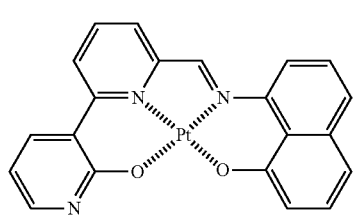
S16
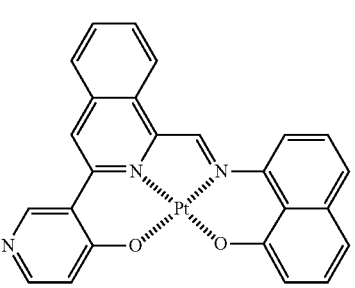

-continued
S17
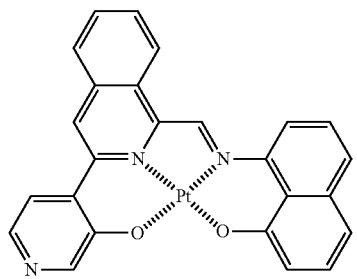
S18
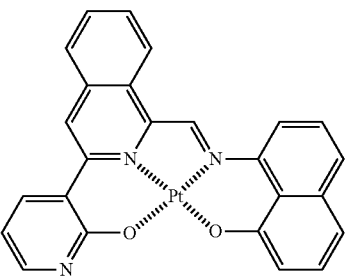
S19
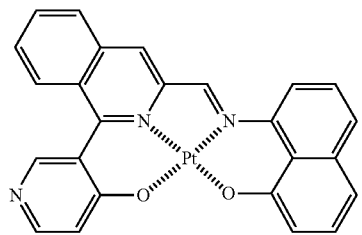
S20
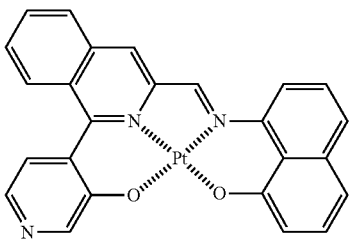
S21
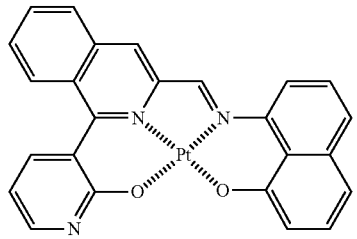
S22
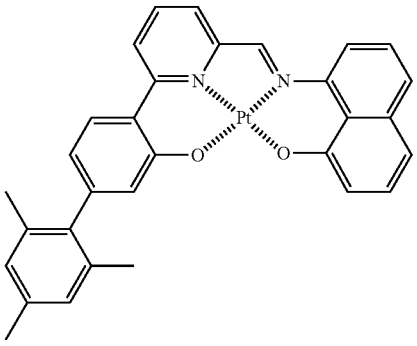
S23
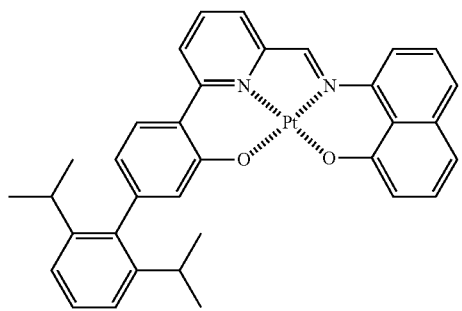
S24
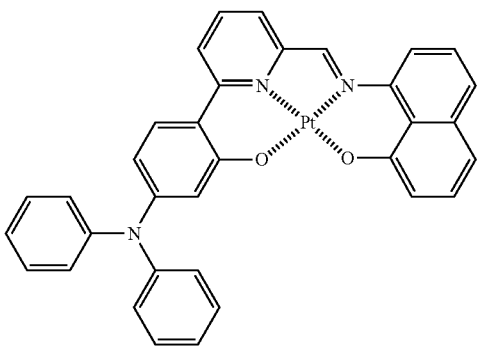
S25
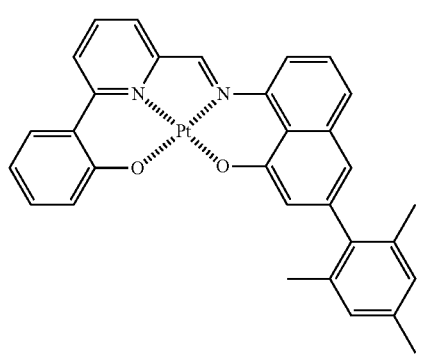
S26
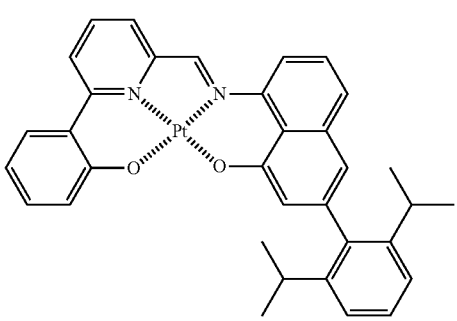

-continued
S27
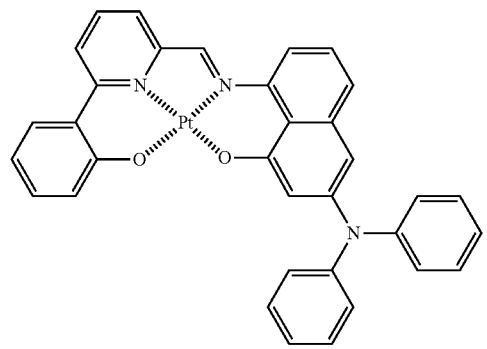
S28
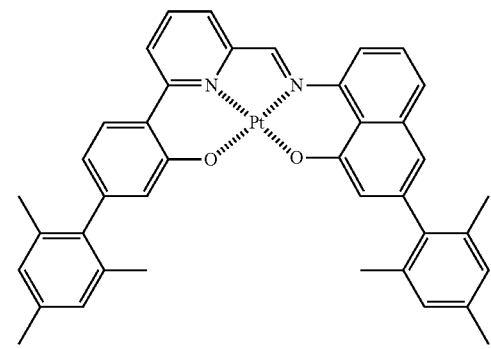
S29
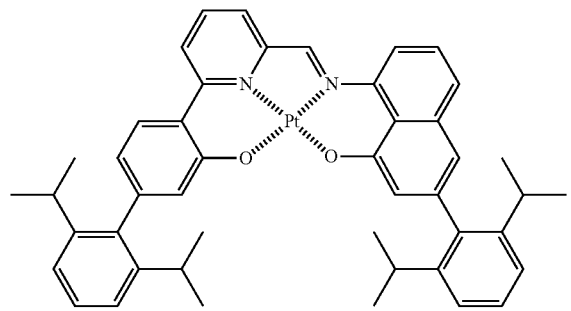
S30
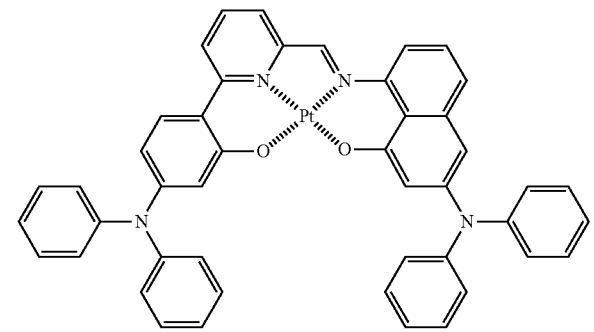
S31
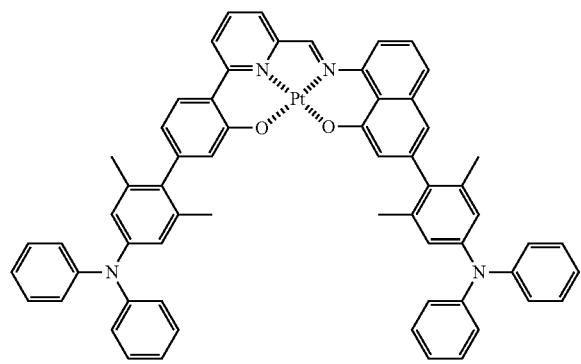
S32
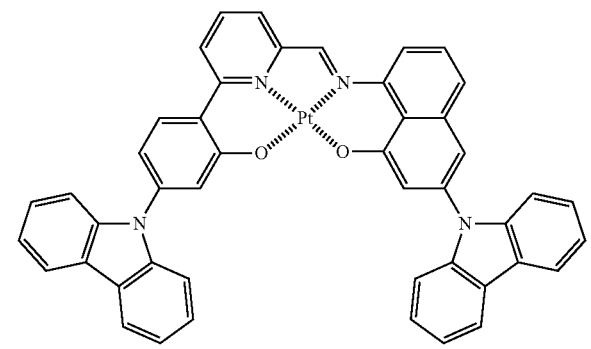
S33
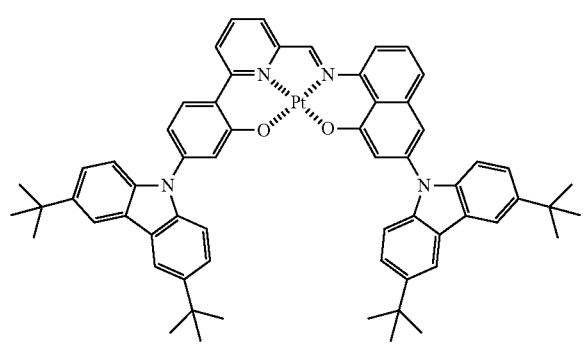

-continued
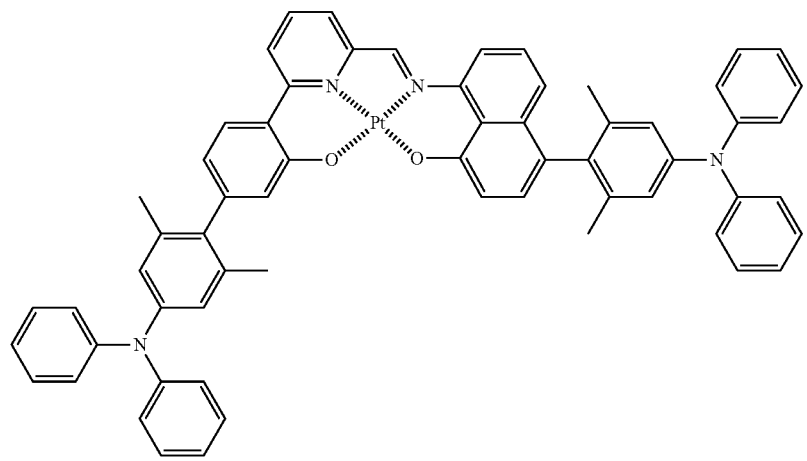
S34
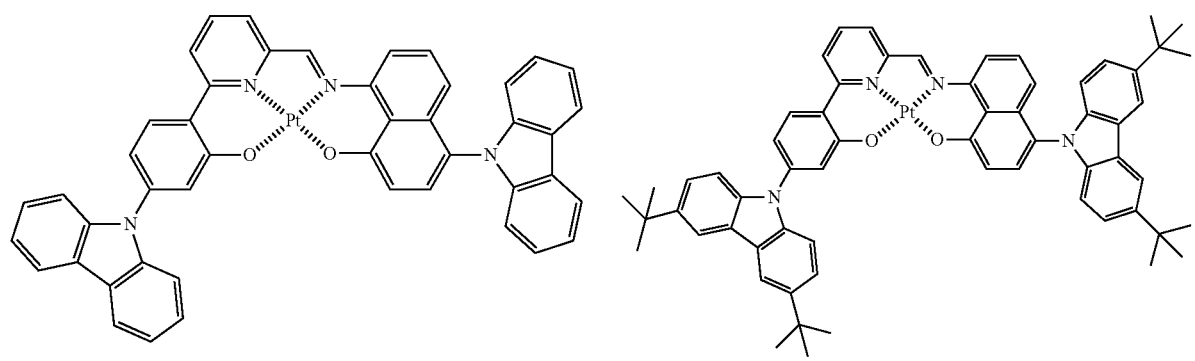
S35
S36
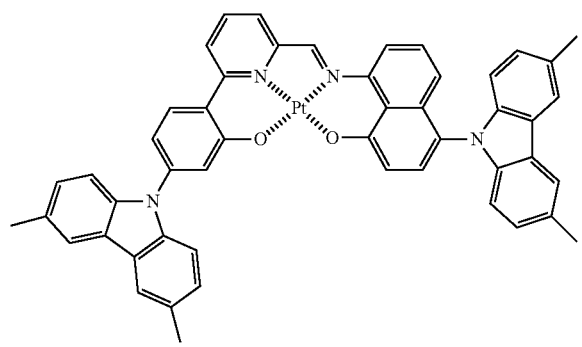
S37
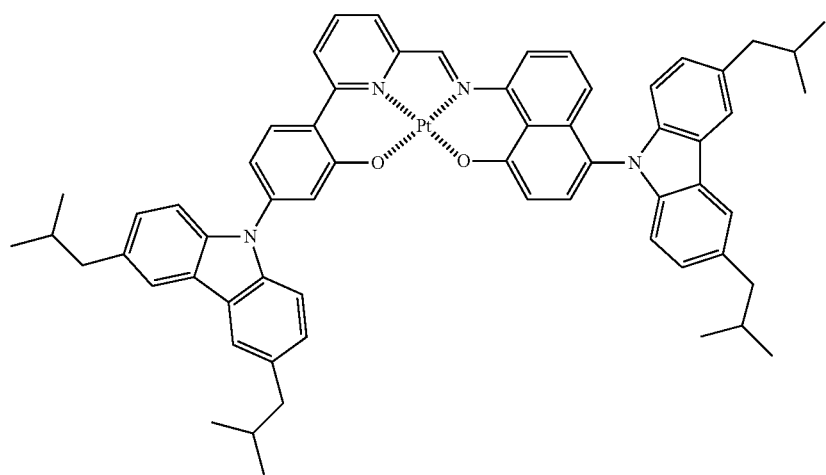
S38

-continued
S39 S40
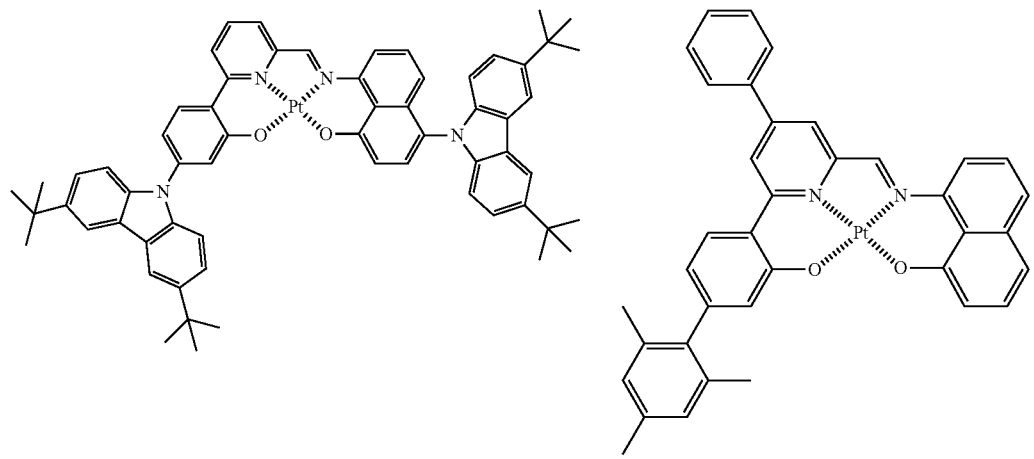
S41 S42
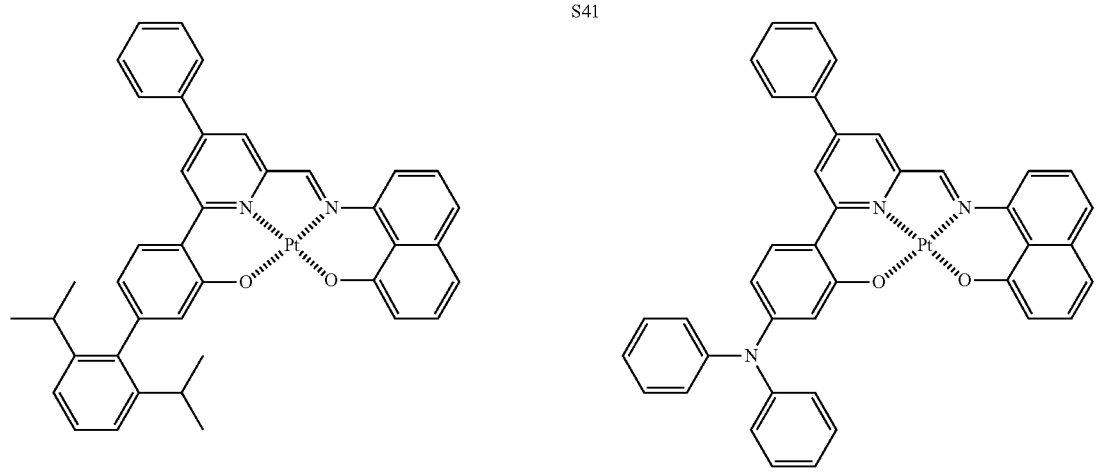
S43 S44
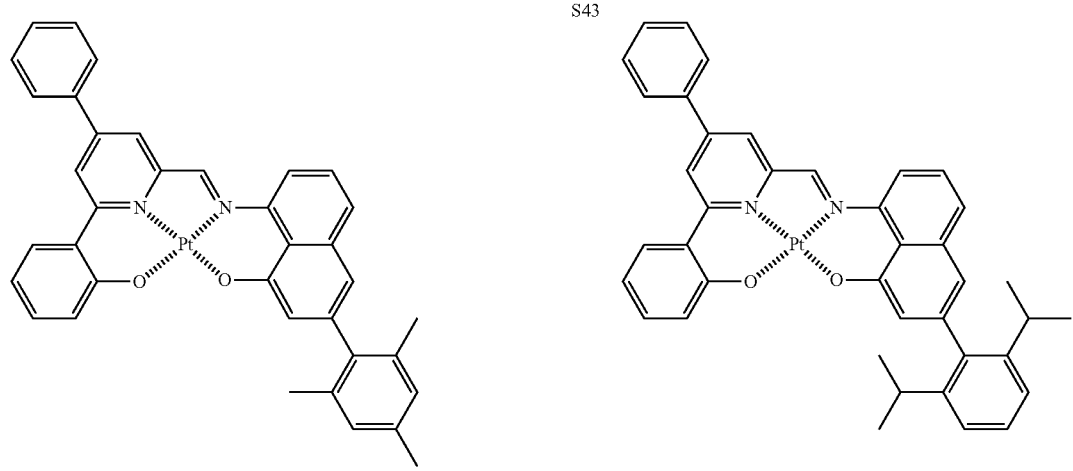

S45
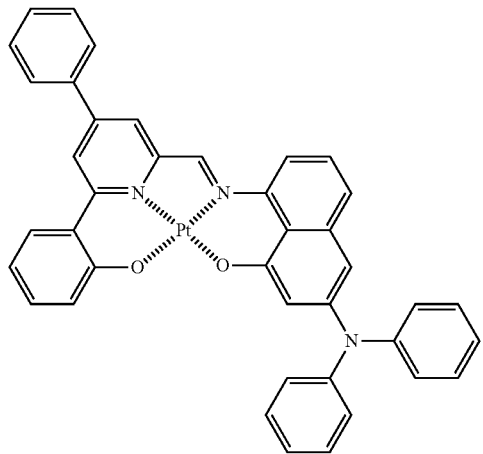
S46
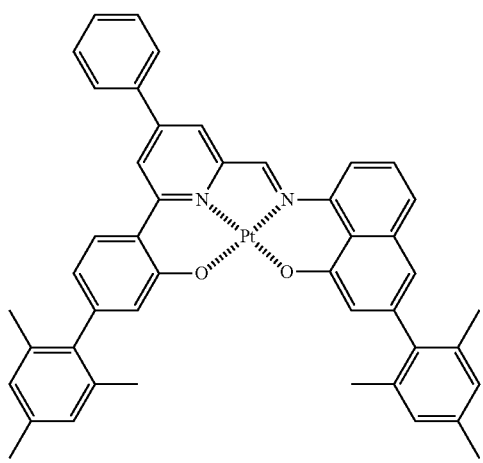
S47
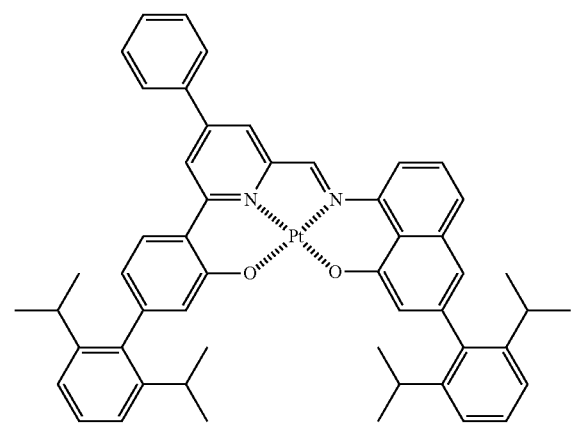
S48
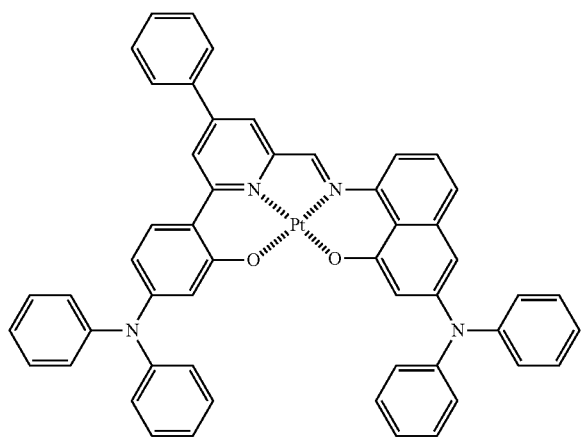
S49
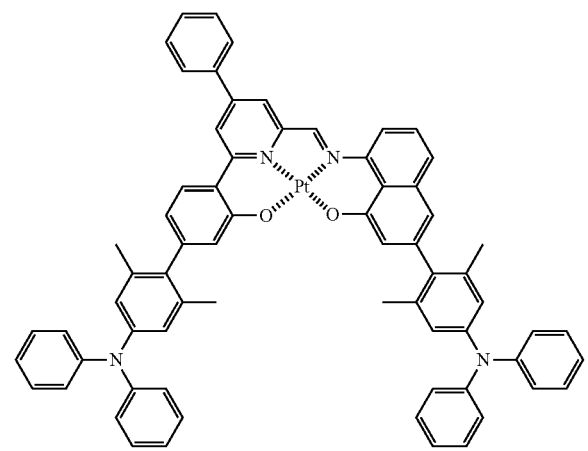

-continued
S50
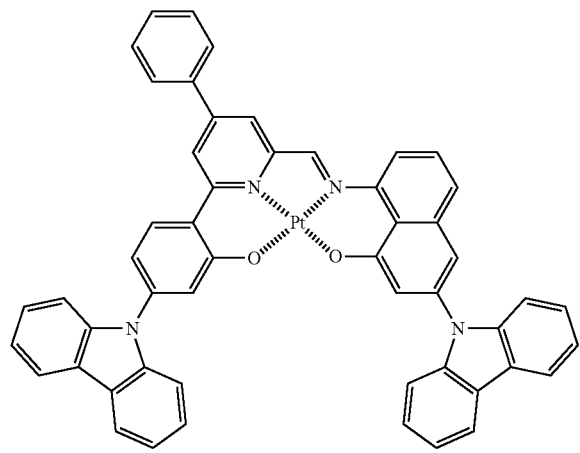
S51
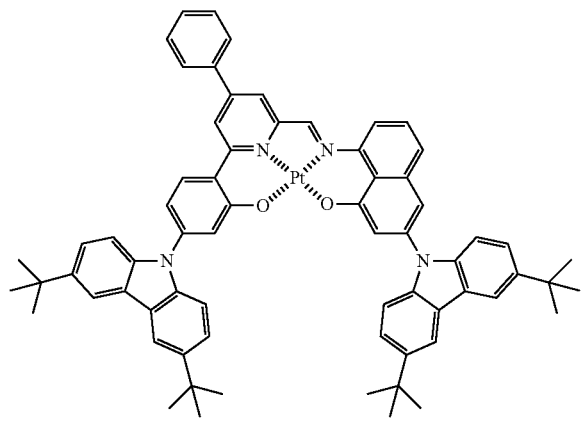
S52
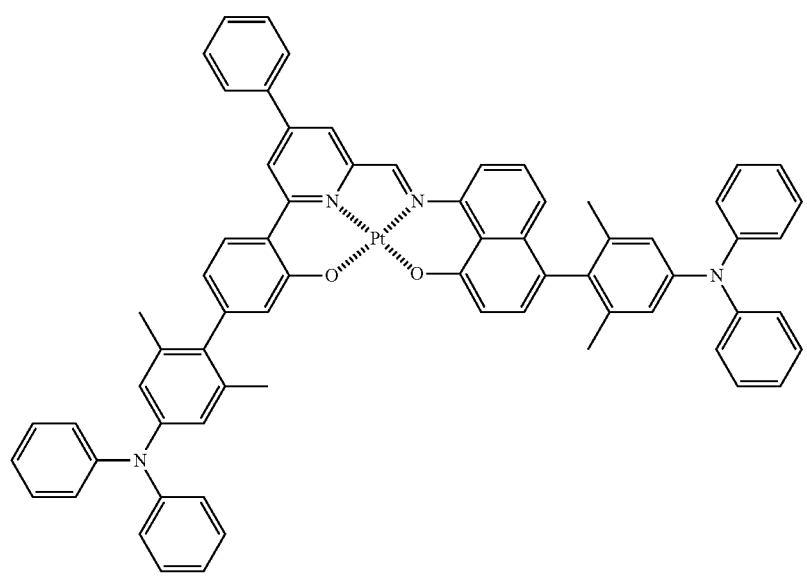
S53
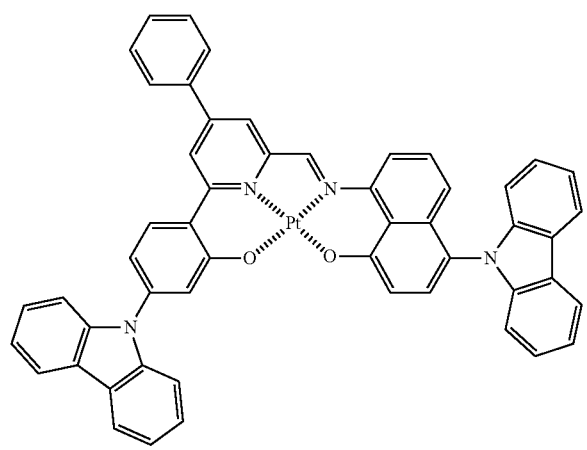
S54
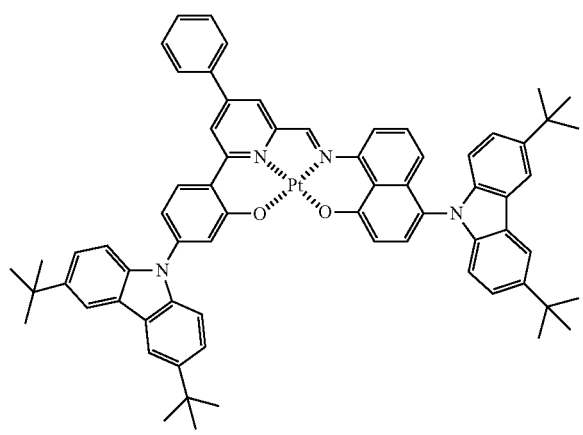

-continued
S55
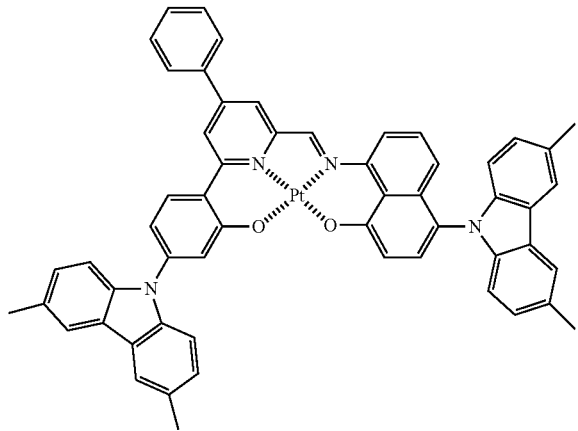
S56
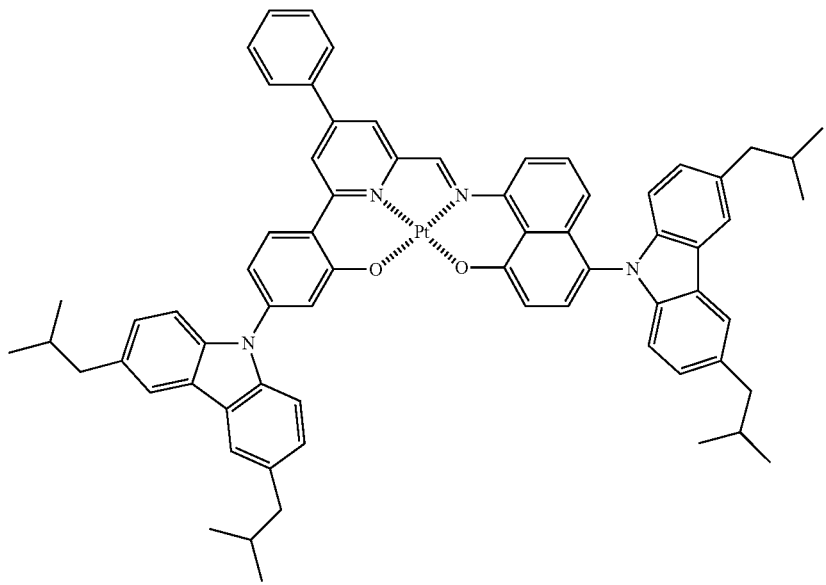
S57
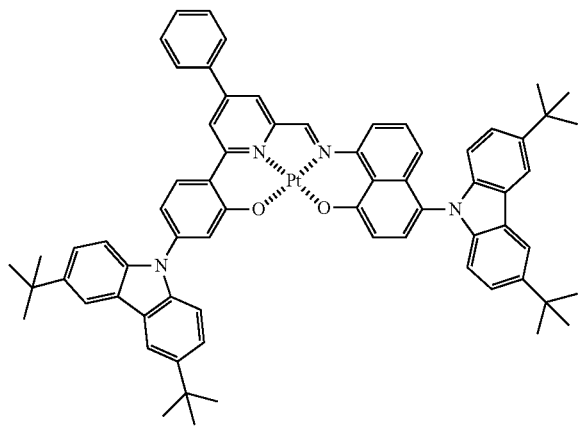
S58
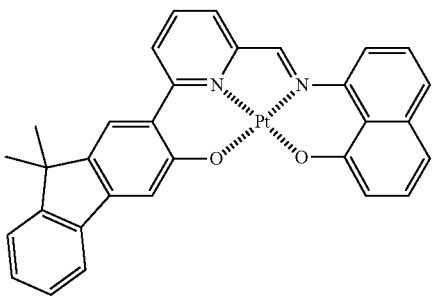

-continued
S59
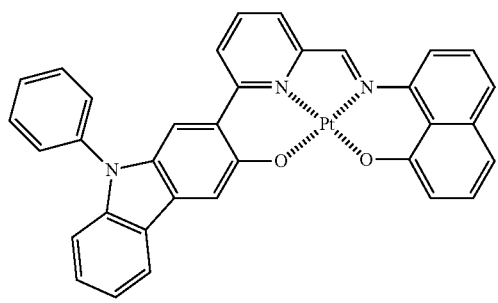
S60
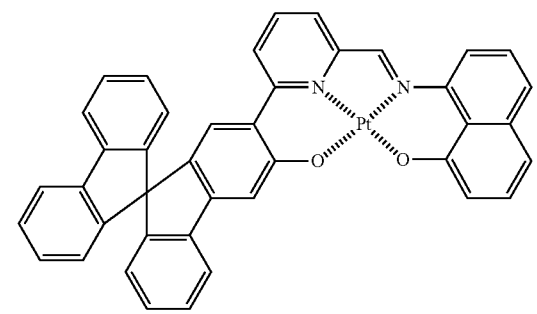
S61
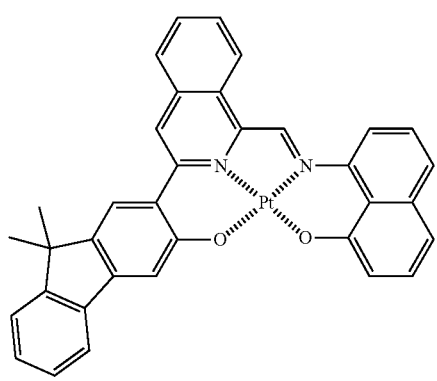
S62
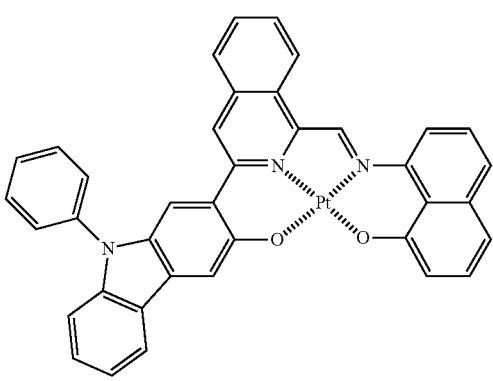
S63
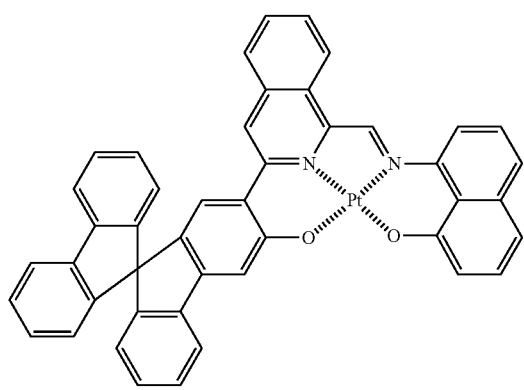
S64
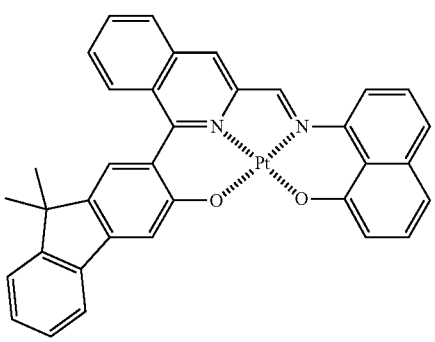
S65
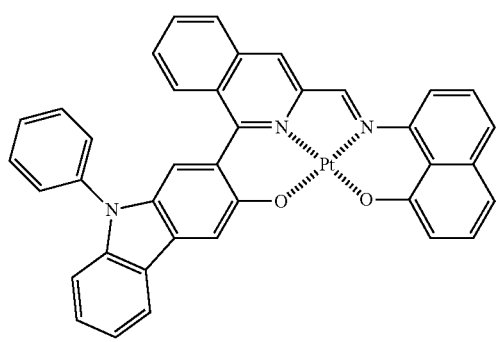
S66
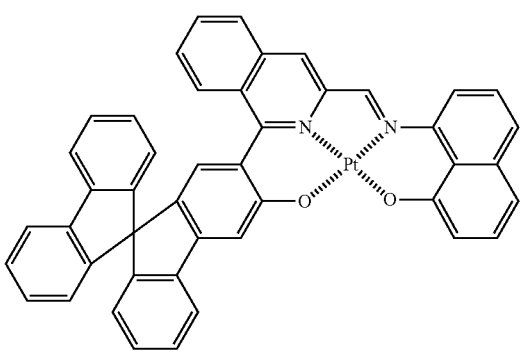

-continued
S67
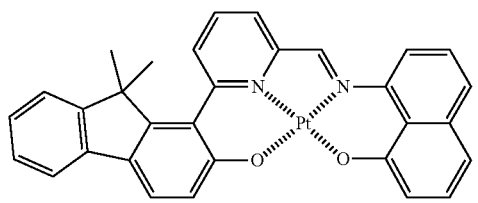
S68
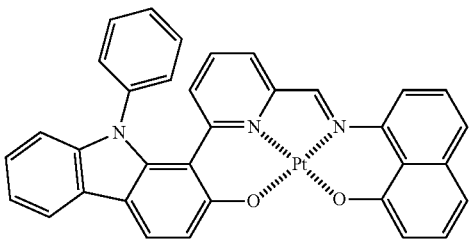
S69
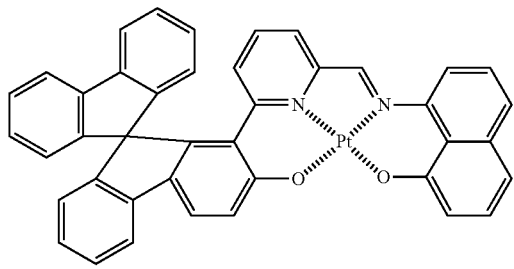
S70
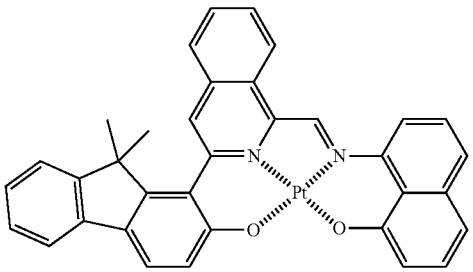
S71
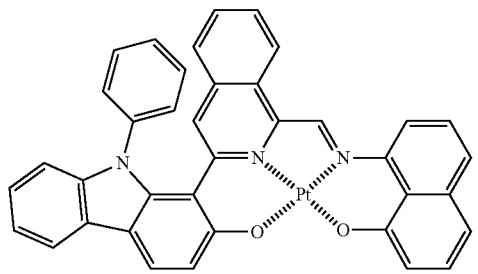
S72
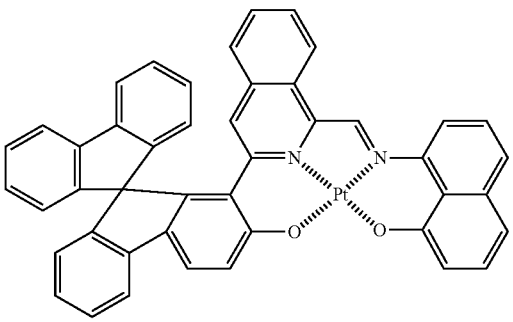
S73
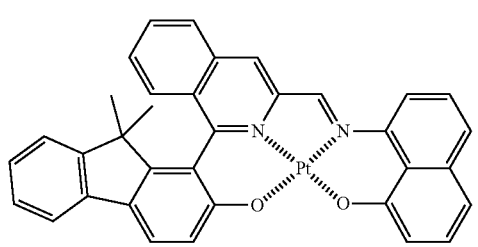
S74
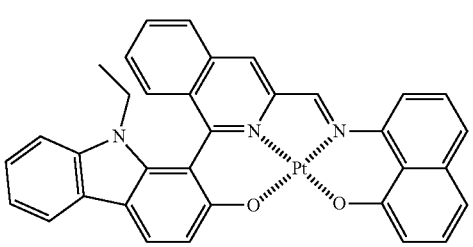
S75
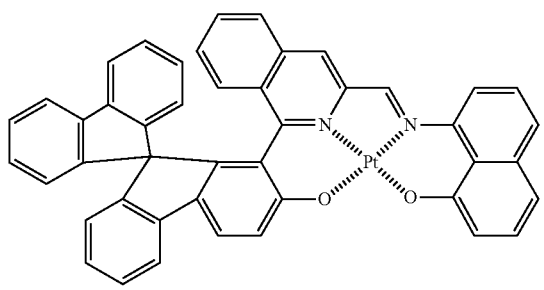
S76
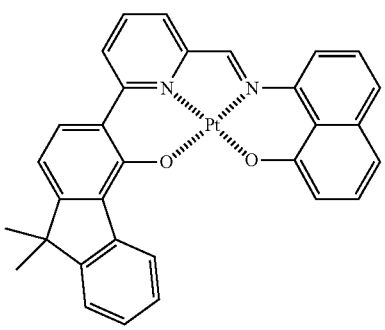

-continued
S77
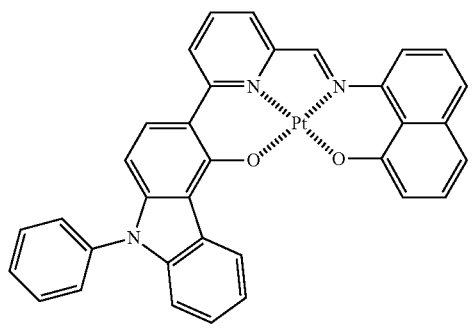
S78
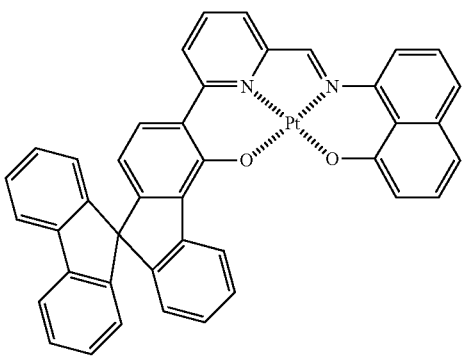
S79
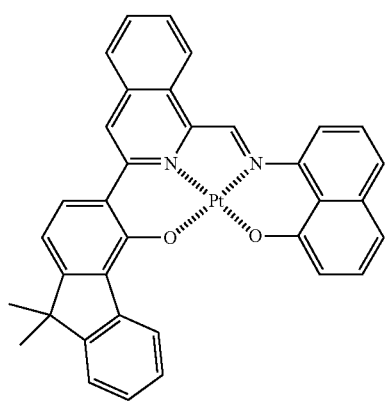
S80
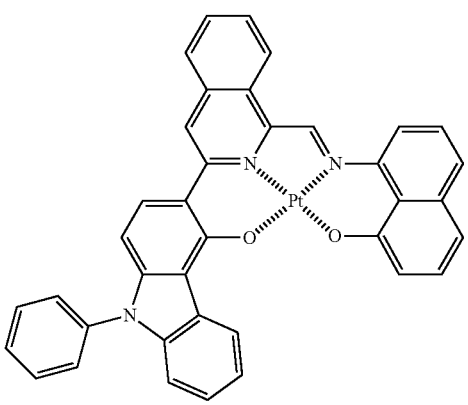
S81
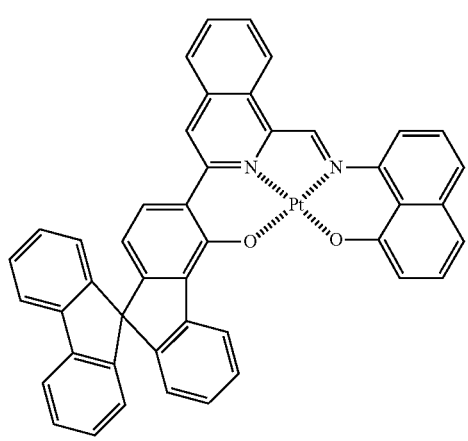
S82
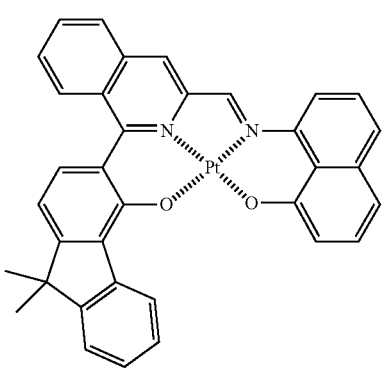
S83
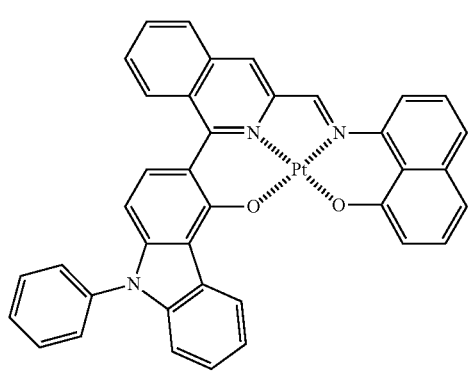
S84
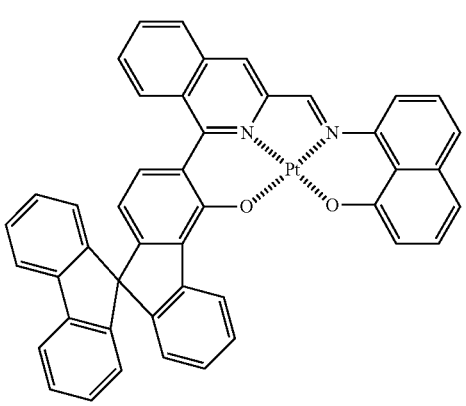

-continued
| S85 | S86 |
|---|---|
| 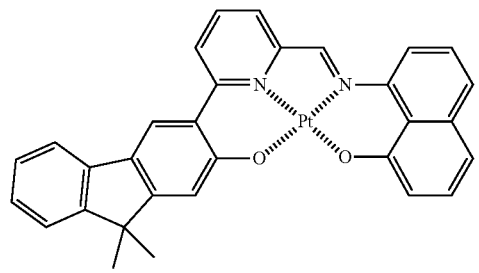 | 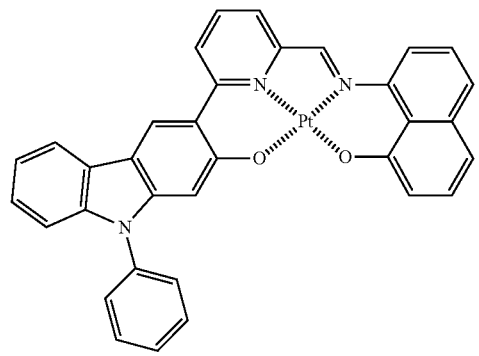 |
| S87 | S88 |
| 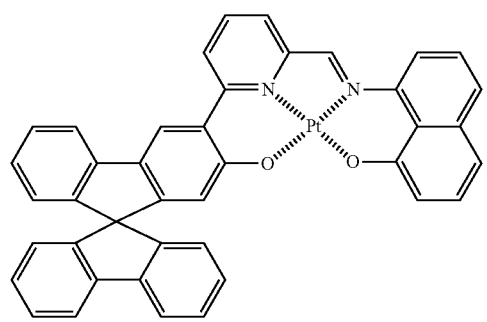 | 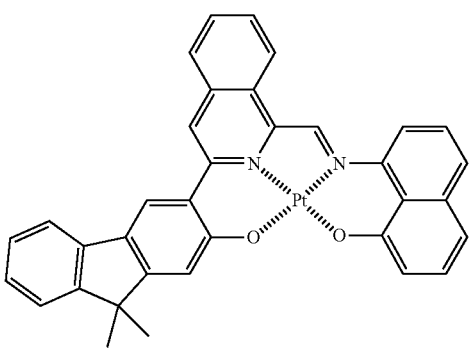 |
| S89 | S90 |
| 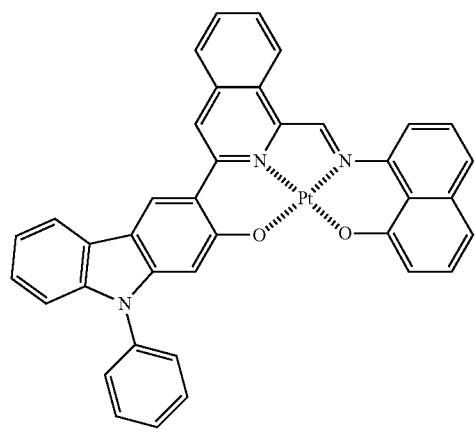 | 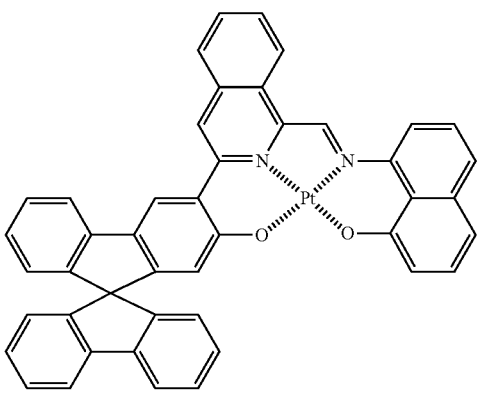 |
| S91 | S92 |
| 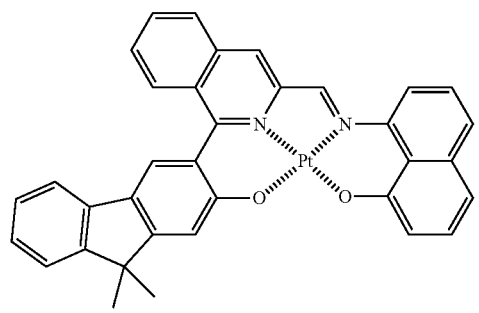 | 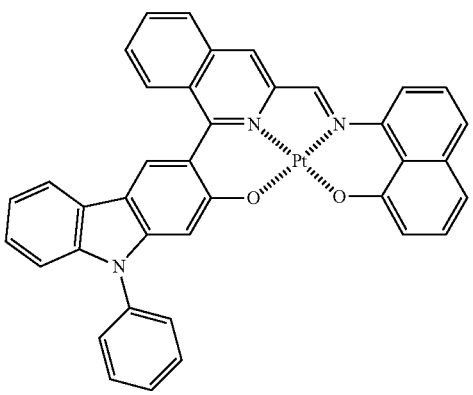 |

-continued
S93
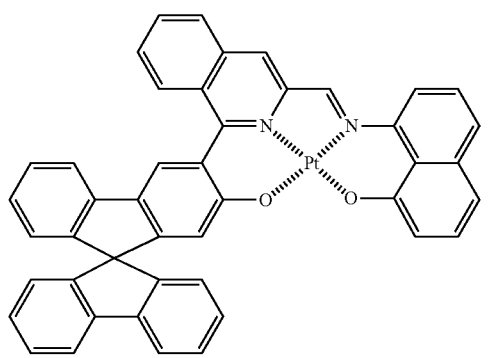
S94
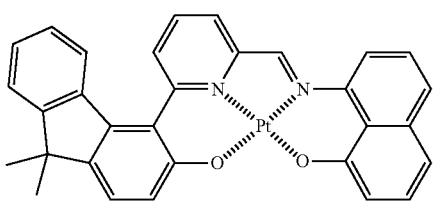
S95
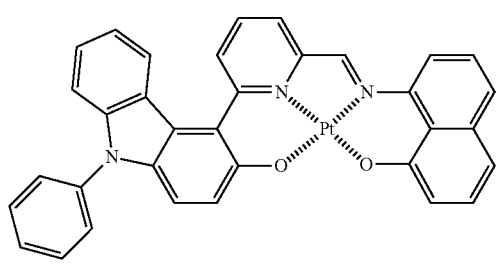
S96
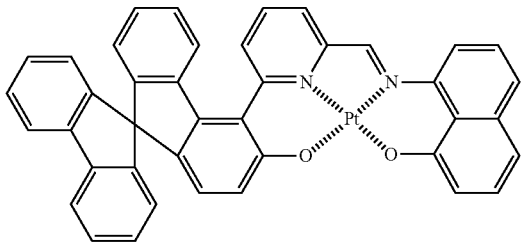
S97
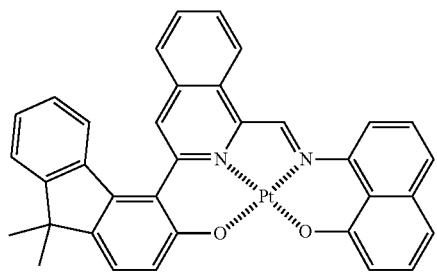
S98
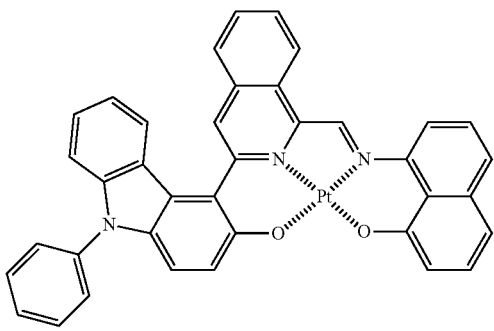
S99
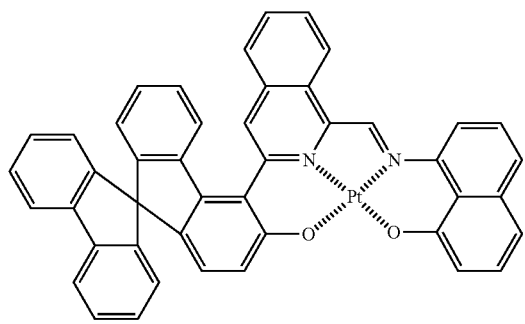
S91
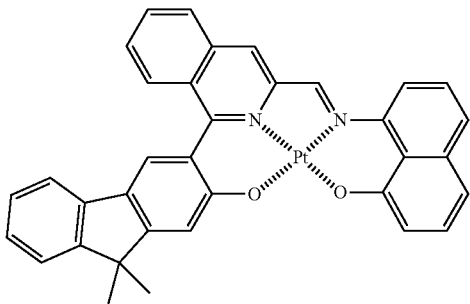
S92
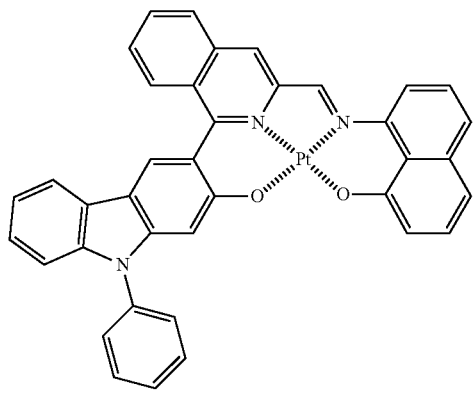
S93
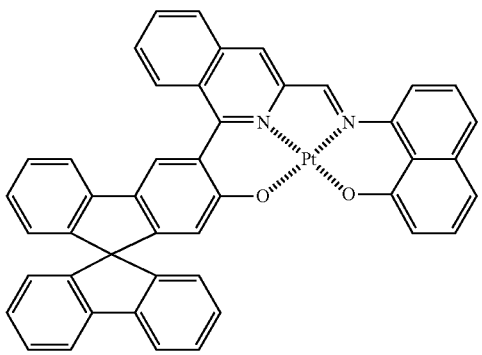

-continued
S94
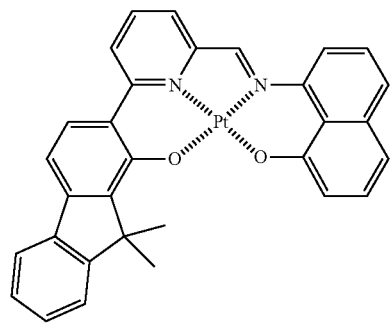
S95
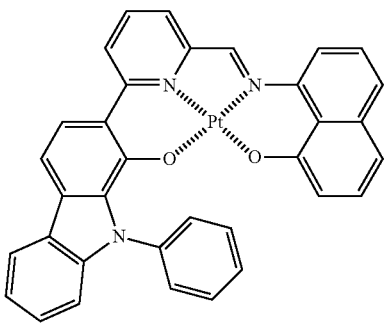
S96
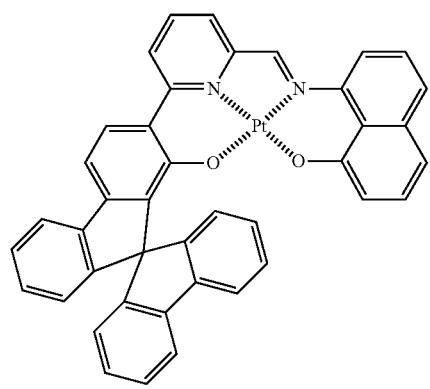
S97
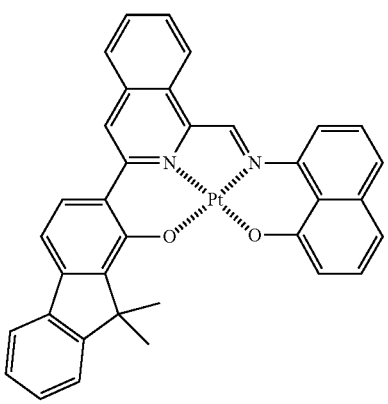
S95
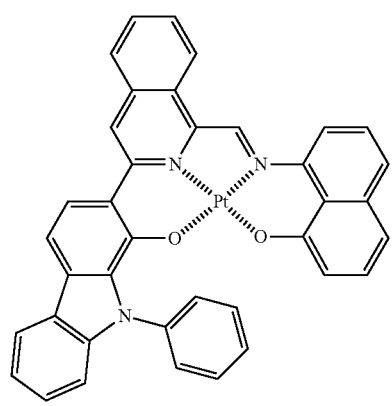
S96
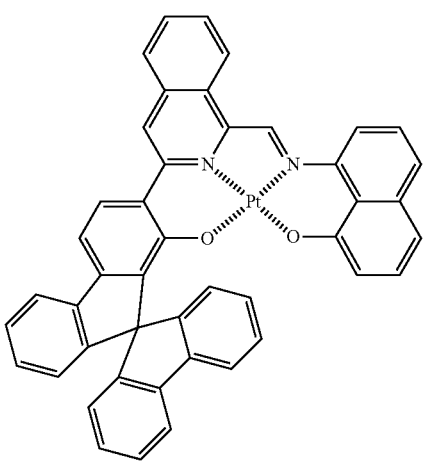
S100
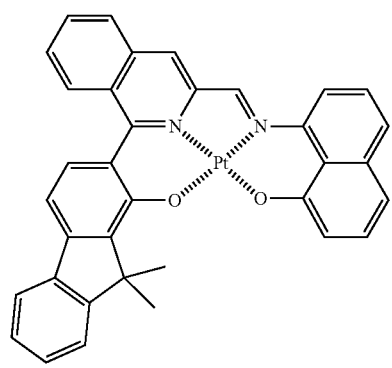
S101
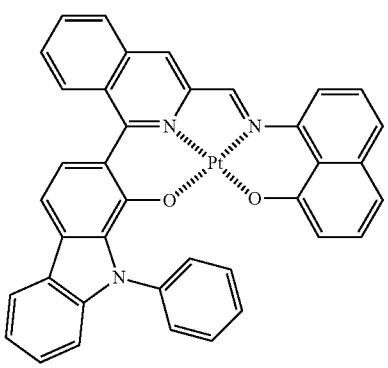

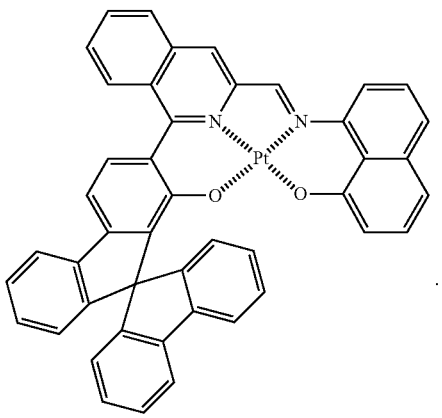

6. The luminescent material according to claim 5, wherein the formula (I) has a structure as shown in Formula (I):

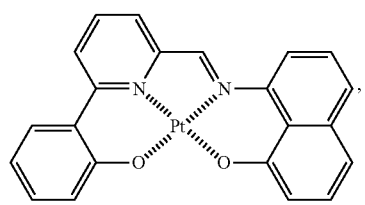
(S1)

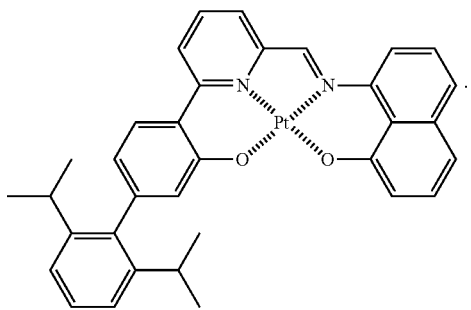
(S23)

7. An application of the luminescent material according to claim 1 in an organic luminescent semiconductor display, organic luminescent semiconductor lighting, solar photovoltaic cells, or organic thin-film semiconductors.

8. An application of the luminescent material according to claim 2 in an organic luminescent semiconductor display, organic luminescent semiconductor lighting, solar photovoltaic cells, or organic thin-film semiconductors.

9. An application of the luminescent material according to claim 3 in an organic luminescent semiconductor display, organic luminescent semiconductor lighting, solar photovoltaic cells, or organic thin-film semiconductors.

10. An application of the luminescent material according to claim 4 in an organic luminescent semiconductor display, organic luminescent semiconductor lighting, solar photovoltaic cells, or organic thin-film semiconductors.

11. An application of the luminescent material according to claim 5 in an organic luminescent semiconductor display, organic luminescent semiconductor lighting, solar photovoltaic cells, or organic thin-film semiconductors.

12. An application of the luminescent material according to claim 6 in an organic luminescent semiconductor display, organic luminescent semiconductor lighting, solar photovoltaic cells, or organic thin-film semiconductors.

* * * * *